United States Patent
Butani et al.

(10) Patent No.: US 11,162,909 B2
(45) Date of Patent: *Nov. 2, 2021

(54) SYSTEM AND METHOD FOR COLORIZING A RADIOGRAPH FROM CABINET X-RAY SYSTEMS

(71) Applicant: KUB Technologies Inc., Stratford, CT (US)

(72) Inventors: Vikram Butani, Stratford, CT (US); Chester Lowe, Stratford, CT (US); Karla Palma, Stratford, CT (US); Peter Yasutake, Stratford, CT (US)

(73) Assignee: KUB Technologies, Inc, Stratford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/186,367

(22) Filed: Feb. 26, 2021

(65) Prior Publication Data

US 2021/0199603 A1 Jul. 1, 2021

Related U.S. Application Data

(63) Continuation-in-part of application No. 16/881,095, filed on May 22, 2020, now Pat. No. 10,937,161.
(Continued)

(51) Int. Cl.
*G01N 23/044* (2018.01)
*G01N 23/083* (2018.01)
(Continued)

(52) U.S. Cl.
CPC ......... *G01N 23/044* (2018.02); *G01N 23/083* (2013.01); *G06T 7/0012* (2013.01);
(Continued)

(58) Field of Classification Search
CPC ....... A61B 6/025; A61B 6/508; G06T 7/0012; G06T 2207/10024; G06T 2207/10112;
(Continued)

(56) References Cited

U.S. PATENT DOCUMENTS

| | | | |
|---|---|---|---|
| 6,236,708 B1 * | 5/2001 | Lin | A61B 6/025 378/22 |
| 7,245,694 B2 * | 7/2007 | Jing | A61B 6/025 378/37 |

(Continued)

*Primary Examiner* — Daniel G Mariam
(74) *Attorney, Agent, or Firm* — Ziegler IP Law Group, LLC

(57) ABSTRACT

A cabinet X-ray image system for obtaining X-ray images and colorized or grey scale density X-ray images of a specimen includes a sampling chamber for containing the specimen, a display, an X-ray system including, an X-ray source, a photon counting X-ray detector, and a specimen platform, and a controller configured to selectively energize the X-ray source, control the photon counting X-ray detector to collect a projection X-ray image of the specimen when the X-ray source is energized, determine the density of different areas of the specimen from data collected from the photon counting X-ray detector of the projection X-ray image, create a density X-ray image of the specimen wherein different areas of the specimen are indicated as a density or range of densities based on the determined density of different areas of the specimen, and selectively display the density X-ray image of the specimen on the display.

30 Claims, 18 Drawing Sheets
(9 of 18 Drawing Sheet(s) Filed in Color)

Typical Example of an X-ray Cabinet System

Related U.S. Application Data

(60) Provisional application No. 62/851,636, filed on May 22, 2019.

(51) Int. Cl.
  *H04N 5/232* (2006.01)
  *H04N 5/272* (2006.01)
  *G06T 7/00* (2017.01)

(52) U.S. Cl.
  CPC ............. *H04N 5/232* (2013.01); *H04N 5/272* (2013.01); *G01N 2223/04* (2013.01); *G01N 2223/401* (2013.01); *G01N 2223/408* (2013.01)

(58) Field of Classification Search
  CPC  G06T 2207/10124; G06T 2207/30024; G16H 6/025; G01N 23/044; G01N 23/083; G01N 2223/401; G01N 2223/408; H04N 5/232; H04N 5/272
  USPC .............................................. 382/128; 348/77
  See application file for complete search history.

(56) References Cited

U.S. PATENT DOCUMENTS

| | | | | |
|---|---|---|---|---|
| 7,831,296 | B2* | 11/2010 | DeFreitas | A61B 6/025 600/427 |
| 2013/0343519 | A1* | 12/2013 | Ma | A61B 6/542 378/54 |
| 2014/0085481 | A1* | 3/2014 | Takahashi | H04N 5/30 348/162 |
| 2015/0297155 | A1* | 10/2015 | Christensen | A61B 6/4078 378/5 |
| 2020/0196975 | A1* | 6/2020 | Vancamberg | G06T 7/0012 |

\* cited by examiner

FRONT VIEW INTO CABINET
Door Open

**Typical Example of an X-ray Cabinet System

View in Sample Chamber with Door Open with
X-ray source at position (14) Top Center

**Lateral View of X-Ray Source
Mounted to Swing Arm at position (14)

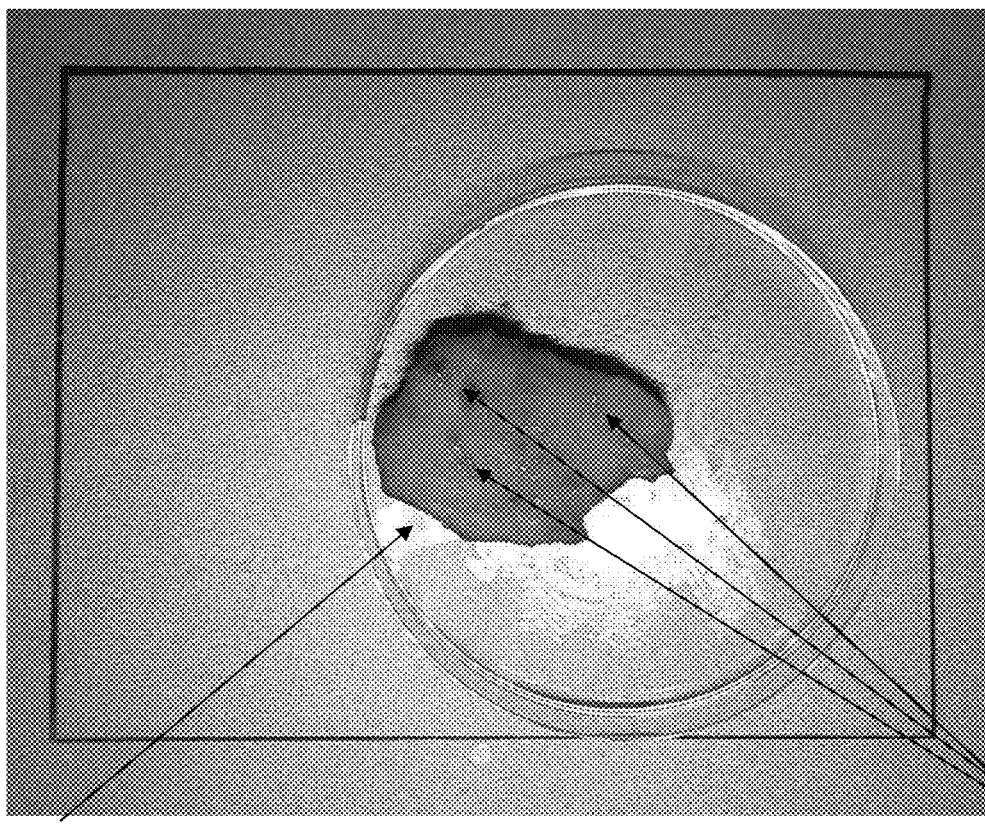
1000  Fig. 10A  1002
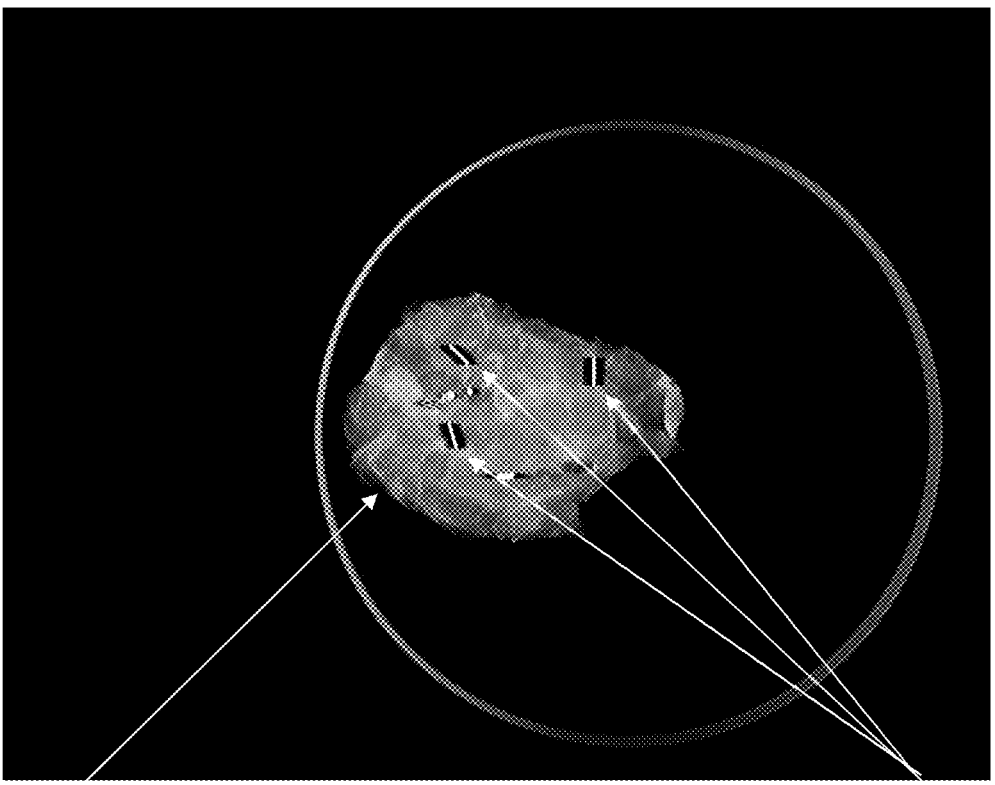
1000  Fig. 10B  1002

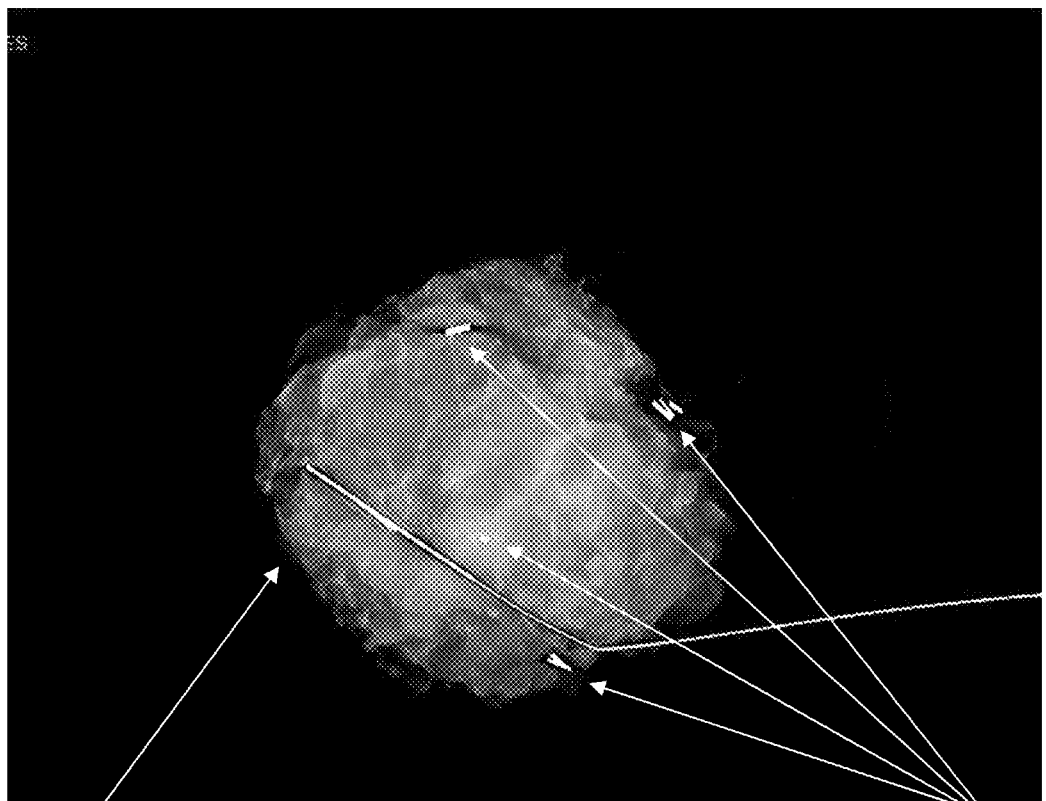
1100  Fig. 11A  1102
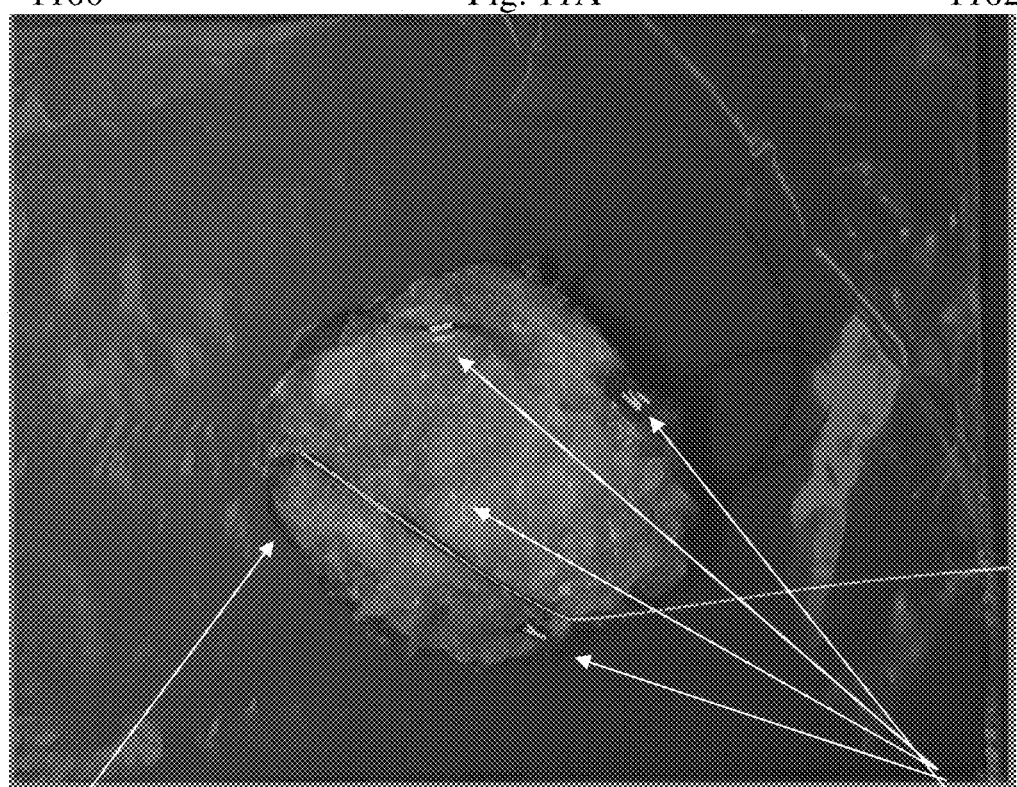
1104  Fig. 11B  1102

SYSTEM AND METHOD FOR COLORIZING A RADIOGRAPH FROM CABINET X-RAY SYSTEMS

CROSS-REFERENCE TO RELATED APPLICATIONS

This application is a Continuation In Part of U.S. patent application Ser. No. 16/881,095 filed May 22, 2020 which claims priority to and the benefit of U.S. Provisional Patent Application Ser. No. 62/851,636 filed May 22, 2019, the disclosures of which are incorporated herein by reference in their entirety.

FIELD OF THE PRESENT DISCLOSURE

The present disclosure relates to a system and method incorporating a cabinet X-ray for taking an X-ray image and displaying the resulting image in a plethora of colors with each color or shade thereof denoting a different density.

BACKGROUND

Today, conventional breast specimen systems can gather a digital breast specimen radiogram and display it in grayscale. In these systems, the radiograms of a tissue or bone specimen are only shown in a grayscale with white distinguishing a very dense item, black distinguishing a non-dense item and various shades of gray distinguishing density level between very dense item and non-dense item, the darker the gray color, the more dense the item.

SUMMARY

With a unit a system and method of colorizing the different densities, a clinician can utilize the resultant image to expeditiously visualize the specimen excised from a patient to confirm orientation of an excised sample saving time for both the patient on the treatment table and the clinician.

It would be advantageous in breast or other specimen acquisition procedures to allow a medical professional such as a clinician, a surgeon. or any type of medical doctor to operate a cabinet X-ray unit to analyze the excised breast tissue or specimen utilizing the unit to capture a multitude of X-ray images taken at different energies or techniques of the sample for informational and/or diagnostic purposes. As a result of processing of the multiple projections, the medical professional could view the images in the same and exact orientation with different colors denoting a density.

A major advantage of color or gray scale resolving X-ray imaging, compared to regular X-ray imaging systems, is the capability to discriminate energy of detected X-rays. This opens the possibility to even recognize different materials in X-ray images. Three or more images may be measured at different energy discrimination thresholds. The images may then analyzed using software tools and a color or gray scale image may be created. Colors or gray scale levels in the image may represent different elements in the sample that are of different densities. The image may then be saved in various formats (e.g., jpeg, .tiff, DICOM, etc.) and resolutions or views and then may be transferred in various resolutions or views in DICOM or any other transmittable format for review.

In this system and method, the resultant X-ray image may be optionally superimposed or overlaid with the optical image. In some cases, the medical professional may only want a faint representation of the optical image blended into the radiographic image while others may wish the optical representation to be more prominent.

Specimen radiography is considered the most cost-effective screening method for the detection of breast cancer in surgically removed breast tissue. However, the sensitivity of specimen radiography is often limited by the presence of overlapping dense fibroglandular tissue in the breast specimen. Dense parenchyma reduces the conspicuity of abnormalities and thus constitutes one of the main causes of missed breast cancer diagnosis. The advent of full-field digital detectors offers opportunities to develop advanced techniques for improved imaging of dense breasts, such as digital tomosynthesis.

In at least one embodiment, the aspects of the present disclosure are directed to a cabinet X-ray incorporating a system and method for taking an X-ray image and displaying the resulting image in a plethora of colors with each color or shade thereof denoting a different density.

In some of the disclosed embodiments, the aspects of the present disclosure are directed to a cabinet X-ray incorporating an X-ray tube, an X-ray detector, and a real-time camera for the production of organic and non-organic specimen images. The computing device receives video data from the real-time camera and the X-ray detector and determines the orientation of the specimen, based on the video data, an overlay of the captured X-ray image with the captured real-time image or display an adjacent image i.e. Picture-In-Picture (PIP). This facilitates and aids the medical professional in ensuring that the proper amount of tissue has been excised. In particular, the disclosure relates to a system and method with corresponding apparatus for capturing a real-time image simultaneously with the X-ray image allowing a cabinet X-ray unit to attain and optimize images with substantially the same or exact orientation of the 2 images as well as utilizing a colorized radiograph for easier distinction.

The radiographic images may be colorized to designate differing densities. In one embodiment, the aspects of the present disclosure are directed to a system and method including a cabinet X-ray system incorporating a real-time camera. This embodiment includes a cabinet X-ray system, a base unit including an image processor and a display, an imaging chain incorporated into the base unit, including an X-ray source with X-ray detector, a system configured to receive video data from the real-time camera, and an interface for enabling an analog/digital signal to be transferred from an image capture apparatus to the image processor of the base unit. The system may be further be configured to supply standard or high-definition (HD) real-time images. A camera can be used to acquire video data and may be digital to provide electronic images. The cabinet X-ray system may concurrently capture an X-ray image and a real-time image. The camera may be mounted onto the system so as to integrate an exact capture/orientation image of the sample being X-rayed. The unit may be enclosed in a cabinet X-ray system. The unit may be utilized for excised tissue, organ or bone specimens. The unit may be utilized for any organic or inorganic specimen that fits inside the system framework or X-ray cabinet. The image capturing mechanism may be mounted in a cabinet X-ray system, such as the cabinet system illustrated in the embodiment shown in FIG. 1. The real-time image can be displayed as overlaid, blended or otherwise combined with the X-ray image either in grayscale or colorized or adjacent to the X-ray image (Picture-in-Picture—PIP). The system may be utilized on two-dimensional (2-D) and three-dimensional (3-D) tomographic radiographs.

In another embodiment, the aspects of the present disclosure are directed to a computing device including at least with one processor and at least one display unit operable by the at least one processor. The at least one display unit operable by the at least one processor is configured to output, for display, determining, based on the video data, a display action and be responsive to determining the preference/initiated action, output for display the resultant images attained by the X-ray cabinet system.

In another embodiment, the aspects of the present disclosure are directed to a cabinet X-ray and optical camera system for obtaining X-ray images and optical images of a specimen. The cabinet X-ray and optical camera system includes a cabinet defining an interior chamber, a display, an X-ray system, an optical camera and a controller. The X-ray system includes an X-ray source, an X-ray detector and a specimen platform. The optical camera is configured to capture an optical image of the specimen. The controller is configured to selectively energize the X-ray source to emit X-rays through the specimen to the X-ray detector, control the X-ray detector to collect a projection X-ray image of the specimen when the X-ray source is energized, selectively display the X-ray image either in grayscale or colorized on the display, control the optical camera to capture and collect the optical image of the specimen and selectively display the optical image on the display.

In another embodiment, the aspects of the present disclosure are directed to a cabinet X-ray and optical camera system for obtaining X-ray images, projection X-ray images, reconstructed tomosynthetic X-ray images and optical images of a specimen. The cabinet X-ray and optical camera system includes a cabinet defining an interior chamber and an equipment enclosure, a display, an X-ray system, an optical camera and a controller. The X-ray system includes an X-ray source positioned in the interior chamber, an X-ray detector positioned in the interior chamber, a specimen platform positioned in the interior chamber and which is a protective cover of and in physical contact with the X-ray detector and a motion control mechanism positioned in the interior chamber and configured for moving the X-ray source to or along a plurality of positions within the interior chamber relative to the specimen disposed on the specimen platform. The optical camera is positioned in the interior chamber and configured to capture an optical image of the specimen. The controller is positioned in the equipment enclosure and configured to selectively energize the X-ray source to emit X-rays through the specimen to the X-ray detector at selected positions of the X-ray source relative to the specimen such that the isocenter of the emitted X-rays at the selected positions is located at a surface of the X-ray detector, control the X-ray detector to collect projection X-ray images of the specimen when the X-ray source is energized at the selected positions, wherein one of the projection X-ray images is a two-dimensional X-ray image taken at standard imaging angle of approximately 0°, create a tomosynthetic X-ray image reconstructed from a collection of projection X-ray images, process the collection of the projection X-ray images in the controller into one or more reconstructed tomosynthetic X-ray images representing a volume of the specimen and relating to one or more image planes that are selectively the same or different from that of the two-dimensional X-ray image, control the optical camera to capture and collect the optical image of the specimen and selectively display at least one of the two-dimensional X-ray image, the one or more reconstructed tomosynthetic X-ray images either in grayscale or colorized and the optical image on the display.

In another embodiment, the aspects of the present disclosure are directed to a method for obtaining an X-ray image and an optical image of a specimen in a cabinet X-ray and optical image system, processing and displaying the X-ray image and optical image of the specimen. The cabinet X-ray and optical image system includes a cabinet defining an interior chamber, a display, an X-ray system, and optical camera and a controller. The X-ray system includes an X-ray source, an X-ray detector and a specimen platform. The optical camera is configured to capture an optical image of the specimen. The controller is configured to selectively energize the X-ray source to emit X-rays through the specimen to the X-ray detector, control the X-ray detector to collect a projection X-ray image of the specimen when the X-ray source is energized, selectively display the X-ray image on the display, control the optical camera to capture and collect the optical image of the specimen and selectively display the optical image on the display. The method includes controlling the X-ray detector to collect an X-ray image of the specimen when the X-ray source is energized, controlling the optical camera to capture and collect the optical image of the specimen and selectively displaying at least one of the X-ray image either in a grayscale or colorized and the optical image on the display.

In one embodiment, a cabinet X-ray image system for obtaining X-ray images and colorized or grey scale density X-ray images of a specimen is provided. The system includes a cabinet defining an interior chamber; a display; an X-ray system (including an X-ray source; an X-ray detector; and a specimen platform); and a controller. The controller is configured to selectively energize the X-ray source to emit X-rays through the specimen to the X-ray detector; control the X-ray detector to collect a projection X-ray image of the specimen when the X-ray source is energized; determine the density of different areas of the specimen from data collected from the X-ray detector of the projection X-ray image of the specimen when the X-ray source is energized; create a density X-ray image of the specimen wherein the different areas of the specimen are indicated as a density or range of densities based on the determined density of different areas of the specimen; and selectively display the density X-ray image of the specimen on the display.

In another embodiment, a cabinet X-ray image system for obtaining colorized or grey scale density tomosynthetic images of a specimen is provided. The system includes a cabinet defining an interior chamber; a display; an X-ray system (including an X-ray source; an X-ray detector; and a specimen platform); a motion control mechanism; and a controller. The motion control mechanism is positioned in the interior chamber and configured for moving the X-ray source to or along a plurality of positions within the interior chamber relative to the specimen disposed on the specimen platform. The controller is configured to selectively energize the X-ray source to emit X-rays through the specimen to the X-ray detector at selected positions of the X-ray source relative to the specimen such that the isocenter of the emitted X-rays at the selected positions is located at a surface of the X-ray detector; control the X-ray detector to collect projection X-ray images of the specimen when the X-ray source is energized at the selected positions, wherein one of the projection X-ray images is a two-dimensional X-ray image taken at standard imaging angle of approximately 0°; determine the density of different areas of the specimen from data collected from the X-ray detector of each of the collection of the projection X-ray images of the specimen collected when the X-ray source is energized; create a collection of density projections X-ray images of the specimen wherein the density of different areas of the specimen based on the determined density of different areas of the specimen for each of the collection of projection X-ray images; create a density tomosynthetic X-ray image reconstructed from the collection of density projection X-ray images using the determined density of different areas of the specimen for the projection X-ray images; process the determined density of different areas of the specimen for the collection of the projection X-ray images in the controller into one or more reconstructed density tomosynthetic X-ray images representing a volume of the specimen and relating to one or more image planes that are selectively the same or different from that of the two-dimensional X-ray image; and selectively display the one or more reconstructed density tomosynthetic X-ray images on the display.

In another embodiment, a method for obtaining X-ray images and colorized or grey scale density X-ray images of a specimen using a cabinet X-ray image system is provided. The cabinet X-ray image system includes a cabinet defining an interior chamber; a display; an X-ray system (including an X-ray source; an X-ray detector; and a specimen platform); and a controller. The controller is configured to selectively energize the X-ray source to emit X-rays through the specimen to the X-ray detector; control the X-ray detector to collect a projection X-ray image of the specimen when the X-ray source is energized; determine the density of different areas of the specimen from data collected from the X-ray detector of the projection X-ray image of the specimen when the X-ray source is energized; create a density X-ray image of the specimen wherein the different areas of the specimen are indicated as a density or range of densities based on the determined density of different areas of the specimen; and selectively display the density X-ray image of the specimen on the display. The method includes controlling the X-ray detector to collect an X-ray image of the specimen when the X-ray source is energized; determining the density of different areas of the specimen from data collected from the X-ray detector of the projection X-ray image of the specimen when the X-ray source is energized; creating a density X-ray image of the specimen wherein the different areas of the specimen are indicated as a density or range of densities based on the determined density of different areas of the specimen; and selectively displaying the density X-ray image of the specimen on the display.

In some of the disclosed embodiments, the X-ray detector may be a photon counting detector controlled to: collect an X-ray image of the specimen when the X-ray source is energized, determine counts of detected photons of different areas of the specimen from the collected X-ray image of the specimen, create a pixelated X-ray image of the specimen wherein the different areas of the specimen are pixelated and the determined counts of detected photons of the different areas are indicated as densities or ranges of densities of the different areas of the specimen, and selectively display the densities or ranges of densities of the different areas of the specimen on the display in a plethora of pre-determined colors corresponding to the densities or ranges of densities of the different areas.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

To further clarify the above and other advantages and features of the present disclosure, a more particular description of the disclosure will be rendered by reference to specific embodiments thereof that are illustrated in the appended drawings. It is appreciated that these drawings depict only typical embodiments of the disclosure and are therefore not to be considered limiting of its scope. The disclosure will be described and explained with additional specificity and detail through the use of the accompanying drawings in which:

FIGS. 10A and 10B—Display an HD view and a radiographic image of a breast specimen utilizing exemplified embodiments of the present disclosure;

FIGS. 11A and 11B—Display a radiographic image and a blended image of a breast specimen utilizing exemplified embodiments of the present disclosure;

DETAILED DESCRIPTION

Figure 1:
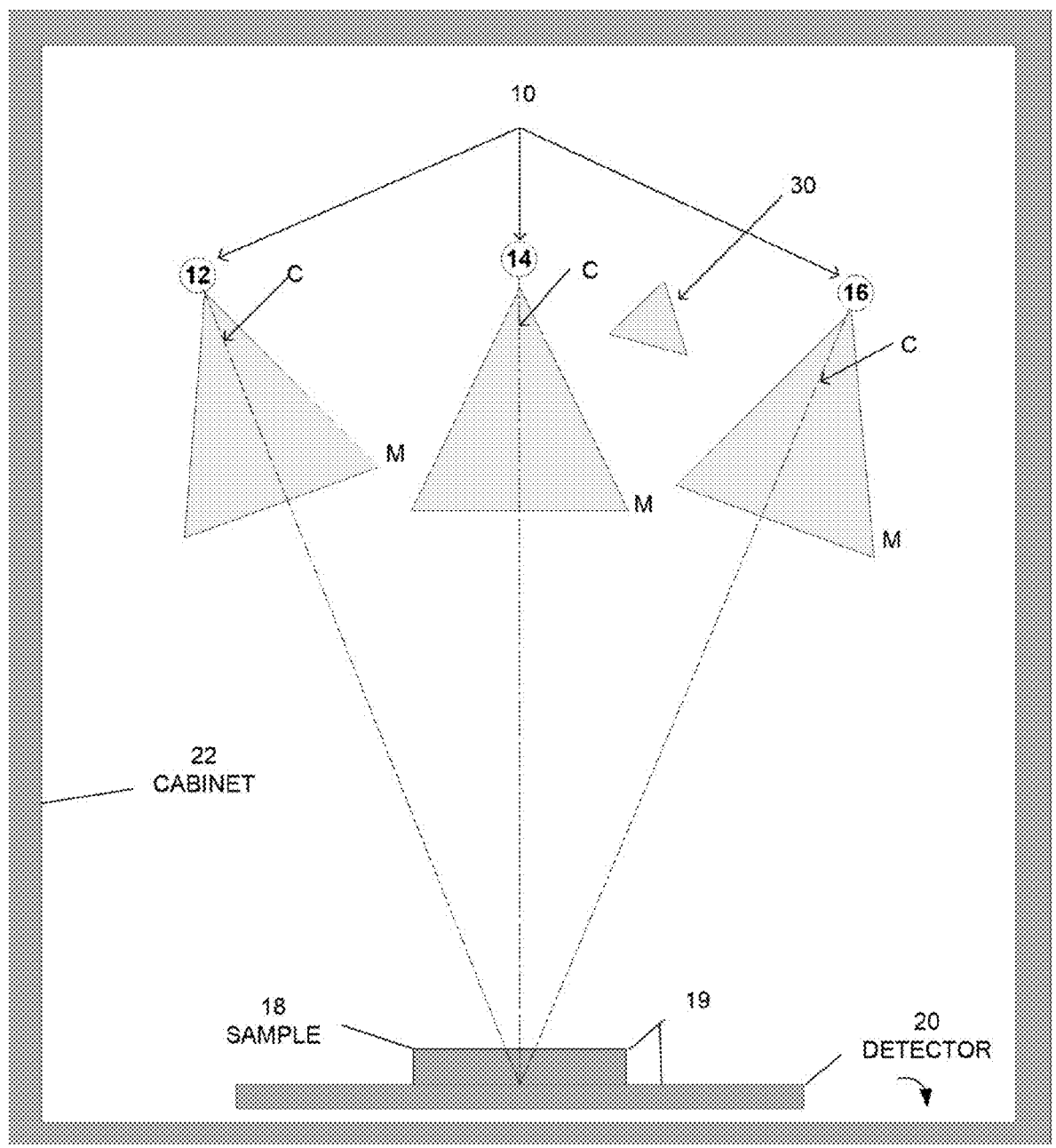
FIG. 1—Schematically illustrates a front view of an X-ray source, a specimen/sample, and a digital detector, where the X-ray source moves relative to the specimen for imaging the specimen at different angles, in one embodiment of a system incorporating aspects of the present disclosure.

In general, aspects of this disclosure include a device (cabinet X-ray system) utilizing an optical camera to capture an optical image of a sample or specimen which is also being X-rayed utilizing a multi-spectral source to produce an X-ray image utilizing a photon-counting X-ray detector, indicating the density of different areas of the sample or specimen, with the resulting 2 images being substantially at the same orientation. The X-ray image can include a two-dimensional (2-D) X-ray image or a synthetic X-ray image assembled from more than one X-ray image (e.g., a tomo-synthetic image). The X-ray image may be colorized or rendered in grayscale to display the differing densities.

The optical image may be displayed on a monitor as overlaid, blended or otherwise combined with the resultant density colorized or gray scale density X-ray image of the sample, as back to back images, side-by-side images, or in a Picture-In-Picture (PIP) format. A device capturing the X-ray image and the optical image of the specimen facilitates confirmation by the medical professional of margins and other features of the specimen once removed from a patient.

In some embodiments, an HD optical camera may be incorporated into a cabinet X-ray unit allowing the system to capture an HD optical image and an X-ray image utilizing an energy integrating or photon-counting X-ray detector, render the X-ray image in color or grayscale, and display the HD optical and X-ray images as disclosed herein.

The present embodiments may be described in the context of specimen radiography, however it should be understood that the disclosed embodiments are not limited to specimen radiography but may utilize other techniques, for example, non-destructive testing, pathology including any radiographic analysis of organic or non-organic samples or specimens. It should also be understood that the disclosed embodiments are not limited to utilizing an HD camera but may utilize any optical camera suitable for use with the disclosed cabinet X-ray system.

Reference will now be made to the drawings wherein like structures will be provided with like reference designations. It is understood that the drawings are diagrammatic and schematic representations of exemplary embodiments of the disclosure and are not limiting of the present disclosure nor are they necessarily drawn to scale. FIGS. 1-17 depict various features and uses of embodiments of the present disclosure, which embodiments are generally directed to a system that can utilize an optical camera, for example, an HD or similar real-time camera, to capture an image of the specimen/sample concurrently with the acquisition of an X-ray image utilizing an energy integrating X-ray detector or, in some embodiments, a photon-counting X-ray detector.

The systems and methods of embodiments of the present disclosure also address unmet needs by providing 2-D X-ray imaging and tomosynthesis apparatus and techniques that include optical imaging for imaging breast specimens that overcome the shortfall of the data received from two-dimensional and tomosynthesis imaging systems alone. The aspects of embodiments of the present disclosure also enable the use of tomosynthesis to efficiently provide accurate three-dimensional imaging of a specimen in which overlapping images having differing attenuation characteristics can be obtained by applying a three-dimensional reconstruction algorithm all in an X-ray cabinet system.

As used herein, the term "computer," "computer system", or "processor" refers to any suitable device operable to accept input, process the input according to predefined rules, and produce output, including, for example, a server, workstation, personal computer, network computer, wireless telephone, personal digital assistant, one or more microprocessors within these or other devices, or any other suitable processing device with accessible memory.

The term "computer program" or "software" refers to any non-transitory machine-readable instructions, program or library of routines capable of executing on a computer or computer system including computer readable program code.

Digital breast specimen tomosynthesis is disclosed in U.S. Patent Publication No. 2015/0131773 (granted as U.S. Pat. No. 9,138,193), Lowe, et al., entitled "SPECIMEN RADIOGRAPHY WITH TOMOSYNTHESIS IN A CABINET," the disclosure of which is hereby incorporated by reference in its entirety.

The overlaying of the radiograph and related disclosure; U.S. Patent Publication No. 2019/0187073, entitled "SYSTEM AND METHOD FOR ATTAINING, SAVING, AND TRANSFERRING A COMBINATION/BLENDED IMAGE FROM CABINET X-RAY SYSTEMS," the disclosure of which is hereby incorporated by reference in its entirety.

The terms "camera" or "optical camera" refer to an instrument, including an optical instrument for capturing images in black and white, gray scale or color using reflected and/or emitted wavelengths of the electromagnetic spectrum, for example, visible light or fluorescent light, from an object, similar to a photograph or that which could be viewed by a human eye, using an electronic light-sensitive sensor array. These terms may include such instruments producing images in standard resolution or HD as well as a digital camera that can directly capture and store an image in computer-readable form using an array of electronic light-sensitive elements—typically semiconductor photo-sensors—that produce a light-intensity-dependent electronic signal in response to being illuminated.

The term "real time camera" refers to a video camera capable of capturing a continuous stream of optical images in real time.

The term "energy integrating detector" refers to a type of pixelated semiconductor detector with photodiodes and thin film transistors arranged in a two dimensional flat panel array that integrate the energy impinging on individual pixels and are polled by supporting circuitry to produce a two dimensional image. In some embodiments, the pixels may include a scintillator for converting X-rays to visible light to enhance sensitivity. Common types of energy integrating detectors may include charge integrating devices such as Complementary metal-oxide-semiconductor (CMOS), direct or indirect detection flat panels (Scintillator screen, Amorphous Silicon (a-Si), Amorphous Selenium (a-Se), and Charge-coupled devices (CCD).

The term "photon counting detector" refers to another type of semiconductor detector that generates a signal or electrical pulse each time a single X-ray photon interacts with a semiconductor material, in contrast with other photodetectors, which may generate a signal proportional to the photon flux impinging on the detector. Electrical charges are generated proportional to the energy of the single photons resulting in transient currents that may be processed by comparators and digital counters. A number of pulses may be counted, giving an integer number of photons detected per measurement period. The counting efficiency may be determined by the quantum efficiency and any electronic losses present in the system. Common types of photon counting X-ray detectors may include photomultipliers, Geiger counters, single-photon avalanche diodes, superconducting nanowire single-photon detectors, transition edge sensors, and scintillation counters. Charge-coupled devices may also sometimes be used as well as hybrid photon counting technology utilizing CMOS or other ASIC technologies.

While in appearance, photon counting detectors may appear similar in technology and packaging to energy integrating detectors, photon counting eliminates gain noise, where the proportionality constant between analog signal out and number of photons varies randomly. Thus, the excess noise factor of a photon-counting detector is unity, and the achievable signal-to-noise ratio for a fixed number of photons will usually be higher than if the same detector were operated without photon counting.

Photon counting can improve temporal resolution. In a conventional detector, multiple arriving photons may generate overlapping impulse responses, limiting temporal resolution to approximately the fall time of the detector. However, if it is known that a single photon was detected, the center of the impulse response can be evaluated to precisely determine the arrival time of the photon.

Specimen tomography is a three-dimensional specimen imaging system. It involves acquiring images of a sample at multiple viewpoints, typically over an arc or linear path. The three-dimensional image is constructed by the reconstruction of the multiple image data set.

One embodiment of a system 100 incorporating aspects of the present disclosure is illustrated in FIG. 1 The system 100 is totally enclosed or housed in an X-ray cabinet 22. In accordance with the aspects of the disclosed embodiments, the X-ray source 10 moves around the stationary sample, 18, typically, but not necessarily, in an arc. References 12, 14, and 16 of FIG. 1 illustrate exemplary positions of the X-ray source 10 within the X-ray cabinet 22. The reference "C" at each of the positions 12, 14, 16 of the X-ray source 10 in FIG. 1 refers to the point source of the X-ray beam. The reference "M" refers to the spread or fan of the X-ray beam.

While the X-ray detector 20 (which can include a digital X-ray detector, a flat X-ray detector and a flat digital X-ray detector) may move or rotate, in accordance with one aspect of the present disclosure, the X-ray detector 20 remains stationary relative to the sample 18 and X-ray source 10 to maintain an equidistant center point. The X-ray data taken at each of a number of exemplary positions 12, 14, 16 of the X-ray source 10 relative to the sample 18 within the X-ray cabinet 22 is processed to form images, where two or more of the differing image positions are utilized to form a digital tomosynthesis image.

In one embodiment, the aspects of the present disclosure limit the arc or linear travel of the X-ray source 10 over about a 20° to about a 50° arc, preferable about 30°, more preferable 20°. The movement can be clockwise or counter clockwise along a path, which includes for example, one or more, or a combination thereof, of the following exemplary ranges: between approximately 350° (reference position 12) to 0° (reference position 14) to 10° (reference position 16), or between approximately 340° (reference position 12) to 0° (reference position 14) to 20° (reference position 16) and or between approximately 335° (reference position 12) to 0° (reference position 14) to 25° (reference position 16). The ranges recited herein are intended to be approximate and inclusive of start and endpoints. In the example of FIG. 1 the X-ray detector 20 is stationary as is the sample 18. The sample 18 also referred to as the "specimen," "object" or "imaging object" is disposed on or rests on the specimen platform 19 (which is a protective cover) or another surface of the X-ray detector 20.

In operation, source 10 is energized to emit an X-ray beam, generally throughout its travel along one or more of the paths or positions described above. The X-ray beam travels through the sample 18 to the X-ray detector 20 and the multiple images collected at varying angles are stored and then utilized for the tomosynthesis reconstruction. The X-ray source 10 may range from about 0 kVp to about 90 kVp, and in some embodiments may be a 50 kVp 1000 µa X-ray source.

Different embodiments of the present disclosure can utilize different ranges of motion of one or more of the X-ray source 10 and X-ray detector 20 as well as changing the angularity of one or both. The inventive aspects of the present disclosure differ from previous systems either the X-ray detector 20 and X-ray source 10 and/or the isocenter is above the sample and the isocenter is not at the detector surface. The isocenter of embodiments of the present disclosure may be positioned at the detector surface, for example, as shown in FIG. 1 where the reference "C" all converge for each of the positions 12, 14, 16 of the X-ray source 10 in FIG. 1. In accordance with the aspects of the present disclosure, in one embodiment, the X-ray source 10 is configured to move, as described herein, while the detector is configured to remain stationary or in a fixed position.

The detector 20 and associated electronics generate image data in digital form for each pixel at each of the angular positions, 12, 14, 16 of X-ray source 10 and translations positions of the detector 20 relative to the sample 18. While only three positions 12, 14, 16 are illustrated in FIG. 1, in practice more images are taken at differing angles. For example, in one embodiment, images can be taken at approximately every 1° of rotation or motion of source 10. The camera 30 represented in the figure may capture an optical image, for example, an HD image of the sample which can be stored with the radiographic images in computer 470.

Figure 2:
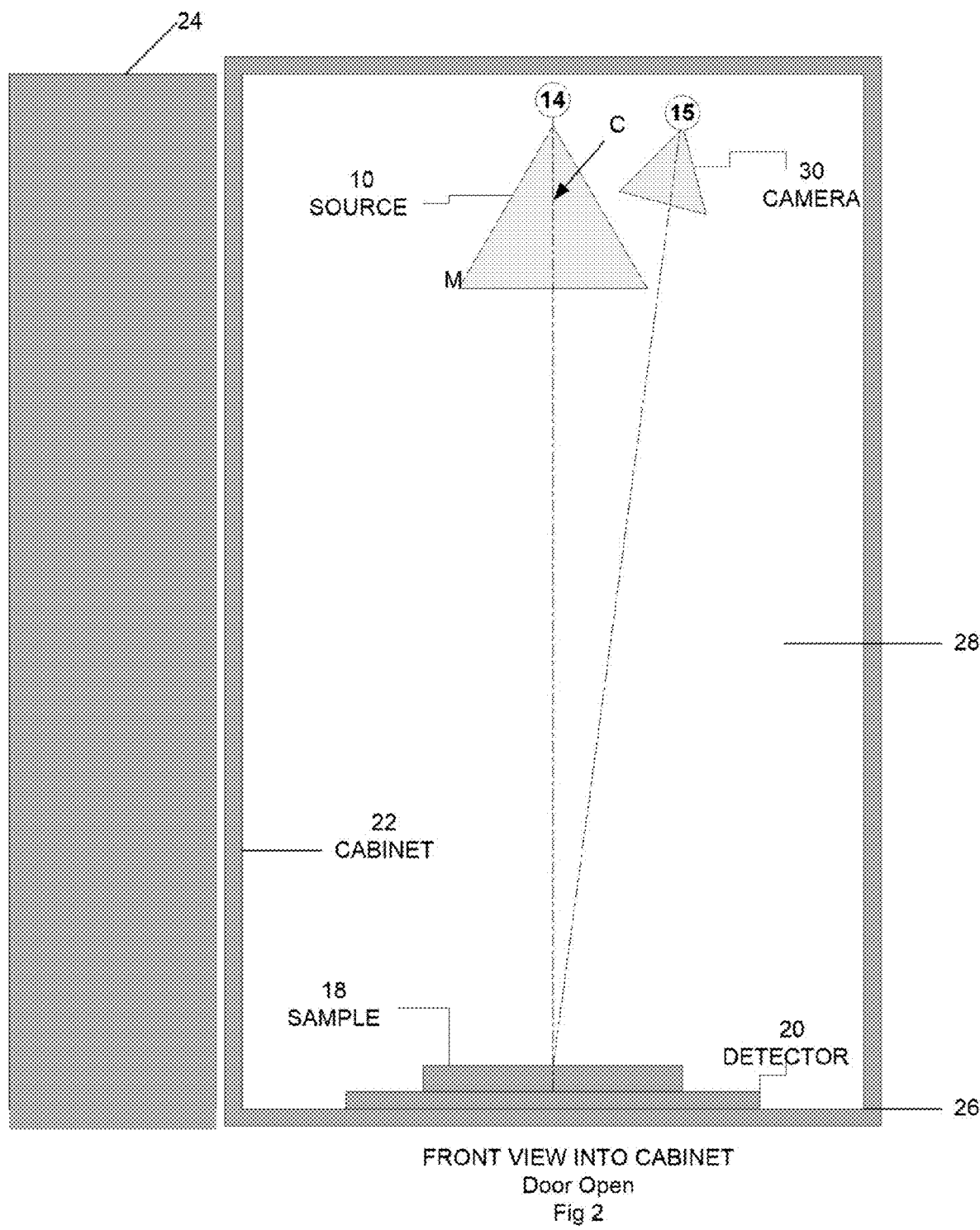
FIG. 2—Schematically illustrates an exemplary orientation of the X-ray source, specimen, and digital detector as viewed when the door of the cabinet is open, in one embodiment of a system incorporating aspects of the present disclosure.

FIG. 2 schematically illustrates one embodiment of the orientation of the X-ray source 10 as seen when the door 24 is opened and the X-ray source 10 is locate at approximately 0°, reference point 14 in this example, within the X-ray cabinet 22. In this embodiment, the motion of the X-ray source 10 can generally occur from the back to the front of the X-ray cabinet 22 with the detector 20 oriented, or otherwise disposed, at the base 26 of the X-ray cabinet 22, within the X-ray cabinet chamber 28. In one embodiment, the detector 20 is suitably coupled to the base 26 of the X-ray cabinet 22. The X-ray spread in this example can be from about 0 kVp to about 50 kVp with the system and may utilize an AEC (Automatic Exposure Control) to ascertain the optimal setting to image the object or sample 18 being examined.

In one embodiment, the detector 20, X-ray source 10, and the swing arm 60 (FIG. 5) servo mechanism are controlled via a combination of one or more of software and hardware, such as non-transitory machine-readable instructions stored in a memory that are executable by one or more processors. On example of such a configuration can include controller cards of a computer 470 (FIG. 4), such as a MS Windows based computer. In one embodiment, non-transitory machine readable instructions being executed by one or more processors of the computer 470 is utilized to compile data received from the detector 20 and present resulting images to a suitable display or monitor 472 (FIG. 4) at each imaging position, such as positions 12, 14 and 16 shown in FIG. 1, the detector 20 generates the respective digital values for the pixels in a two-dimensional array. The size of detector 20 may range, for example, from about 5.08 centimeters by 5.08 centimeters to about 40.64 centimeters by 40.64 centimeters, and in some embodiments may measure about 12.7 centimeters by 15.24 centimeters. In one example, detector 20 has a rectangular array of approximately 1536×1944 pixels with a pixel size of 74.8 micrometers. The image dataset attained at each respective position may be processed either at the full spatial resolution of detector 20 or at a lower spatial resolution by overlapping or binning a specified number of pixels in a single combined pixel value.

For example, if we bin at a 2×2 ratio, then there would be an effective spatial resolution of approximately 149.6 micrometers. This binning may be achieved within the original programming of the detector 20 or within the computer 470 providing the tomosynthetic compilation and image.

Figure 3:
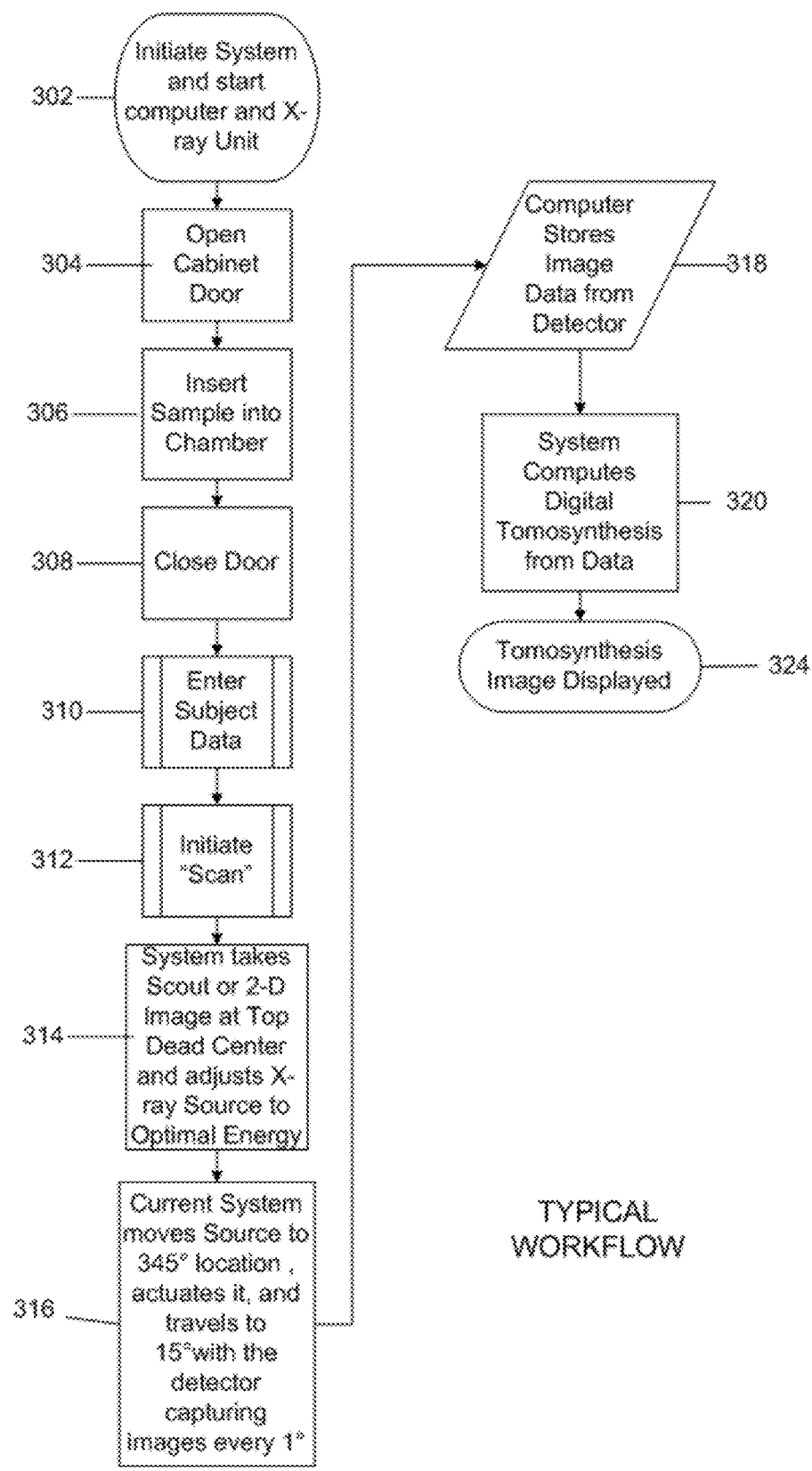
FIG. 3—Displays an exemplary workflow/flowchart of an aspect of the disclosed embodiments.

FIG. 3 illustrates one embodiment of an exemplary workflow from initiating 302 the system 100 through imaging, reconstruction and display 324 of data images collected of the sample 18.

As will be generally understood, the system 100 is initiated 302, the X-ray cabinet door 24 opened 304, and the sample 18 placed into 306 the X-ray cabinet chamber 28. As shown in FIG. 2, for example, the sample 18 is positioned on the detector 20 in a suitable manner. The door 24 is closed 308.

The data and information regarding the sample 18, including any other suitable information or settings relevant to the imaging process and procedure, is entered 310 into the computer 470. The scan is initiated 312. The system 100 will take 314 scout or 2-D images at Top Dead Center, which for purposes of this example is position 14 of FIGS. 1 and 2. The X-ray source 10 can then be moved to other positions using, for example, the swing arm 60 (FIG. 5) with servo mechanism (the latter connected to and motion controlled by, for example, computer 470) to which the X-ray source is mounted, such as positions 12 and 16, and the detector 20 can be used to capture 316 images at various increments along the travel path of the X-ray source 10, such as about every 1 degree.

The captured images are stored 318 and digital tomosynthesis is performed 320. The tomosynthesis image is then displayed 324.

Other embodiments of a system 100 incorporating aspects of the present disclosure are illustrated in FIGS. 1 and 2 where system 100 is totally enclosed or housed in an X-ray cabinet 22 and the X-ray source 10 is stationary relative to the stationary sample, 18 and can be used to obtain a 2-D image. In these embodiments, X-ray source 10 can be positioned at position 14 and the reference "C" refers to the point source of the X-ray beam and the reference "M" refers to the spread or fan of the X-ray beam. While the detector 20 may move or rotate, in accordance with one aspect of the present disclosure, the detector 20 can remain stationary relative to the sample 18 and X-ray source 10 to maintain an equidistant center point. The sample 18 also referred to as the "specimen," "object" or "imaging object" may be disposed on or rest on the specimen platform 19 (which is a protective cover) or another surface of the detector 20. As with the previous embodiments described herein, the inventive aspects of the present disclosure differ from the prior art in that in prior art systems either the detector and X-ray source 10 and/or the isocenter is above the sample and not at the detector surface. In operation, source 10 is energized to emit an X-ray beam at position 14, located at approximately 0°, and thereby obtain a 2-D image of sample 18. In operation, source 10 is energized to emit an X-ray beam, generally throughout its travel along one or more of the paths or positions described above. The X-ray beam travels through the sample 18 to the detector 16 and a 2-D image is stored. The X-ray source 10 may range from about 0 kVp to about 90 kVp, and in some embodiments may be a 50 kVp 1000 μa X-ray source.

Figure 4:
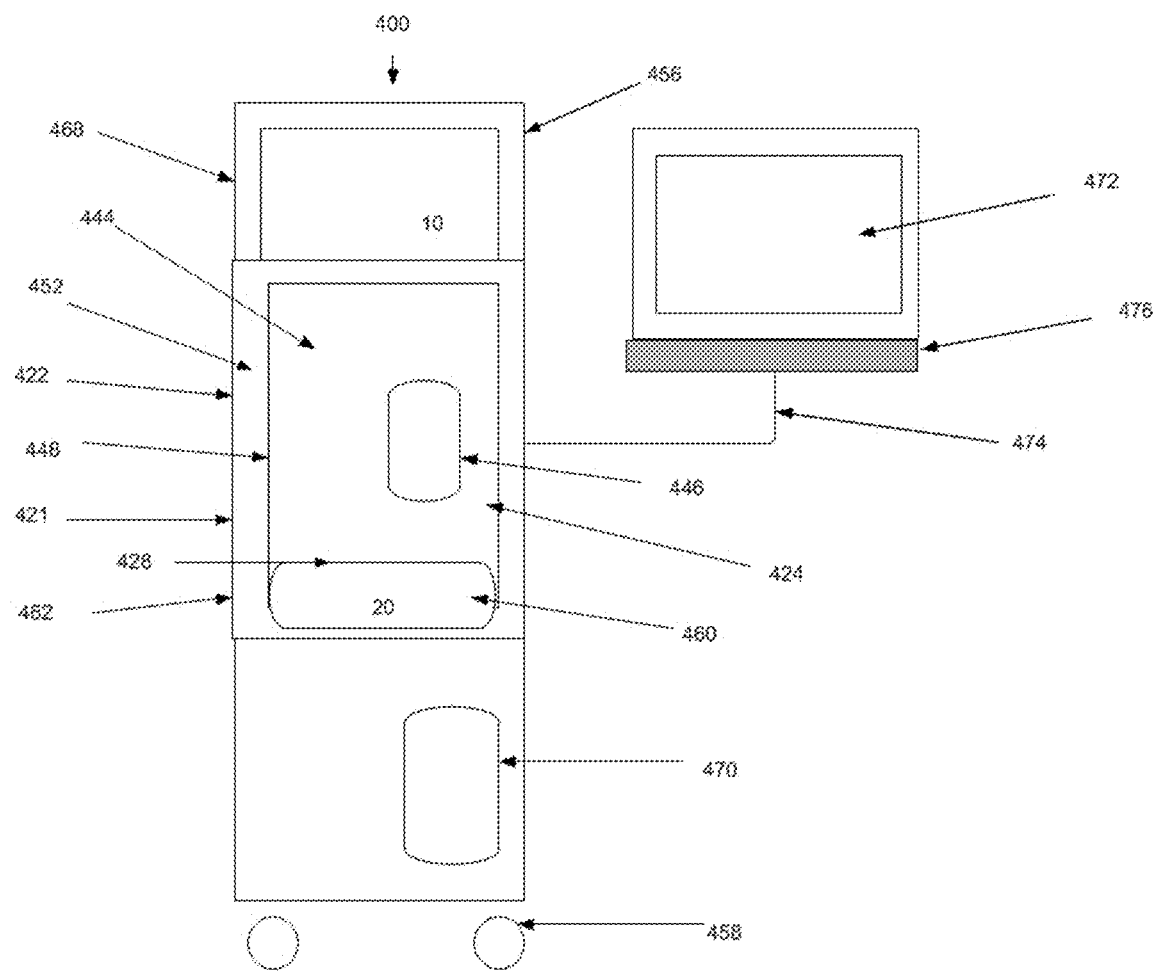
FIG. 4—Displays an example of an X-ray Cabinet System incorporating aspects of the present disclosure.

FIG. 4 shows one embodiment of an X-ray Cabinet System 400 incorporating aspects of the present disclosure. In this embodiment, the X-ray Cabinet System 400 is mounted on wheels 458 to allow easy portability. In alternate embodiments, the X-ray Cabinet System 400 can be mounted on any suitable base or transport mechanism. The cabinet 422 in this example, similar to the exemplary X-ray cabinet 22 of FIG. 1, is constructed of a suitable material such as steel. In one embodiment, the cabinet 422 comprises painted steel defining a walled enclosure with an opening or cabinet chamber 428. Within the cabinet chamber 428, behind door 424, resides an interior space forming a sample chamber 444, which in this example is constructed of stainless steel. Access to the sample chamber 444 is via an opening 446. In one embodiment, the opening 446 of the sample chamber 444 has a suitable door or cover, such as a moveable cover 448. In one embodiment, the moveable cover 448 comprises a door which has a window of leaded glass.

Between the outer wall 421 of cabinet 422 and the sample chamber 444 are sheets of lead 452 that serve as shielding to reduce radiation leakage emitted from the X-ray source 10. In the example of FIG. 4, the X-ray source 10 is located in the upper part 456 of the cabinet 422, in the source enclosure 468. The detector 20 is housed in the detector enclosure 460 at an approximate midpoint 462 of the cabinet 422.

Figure 5:
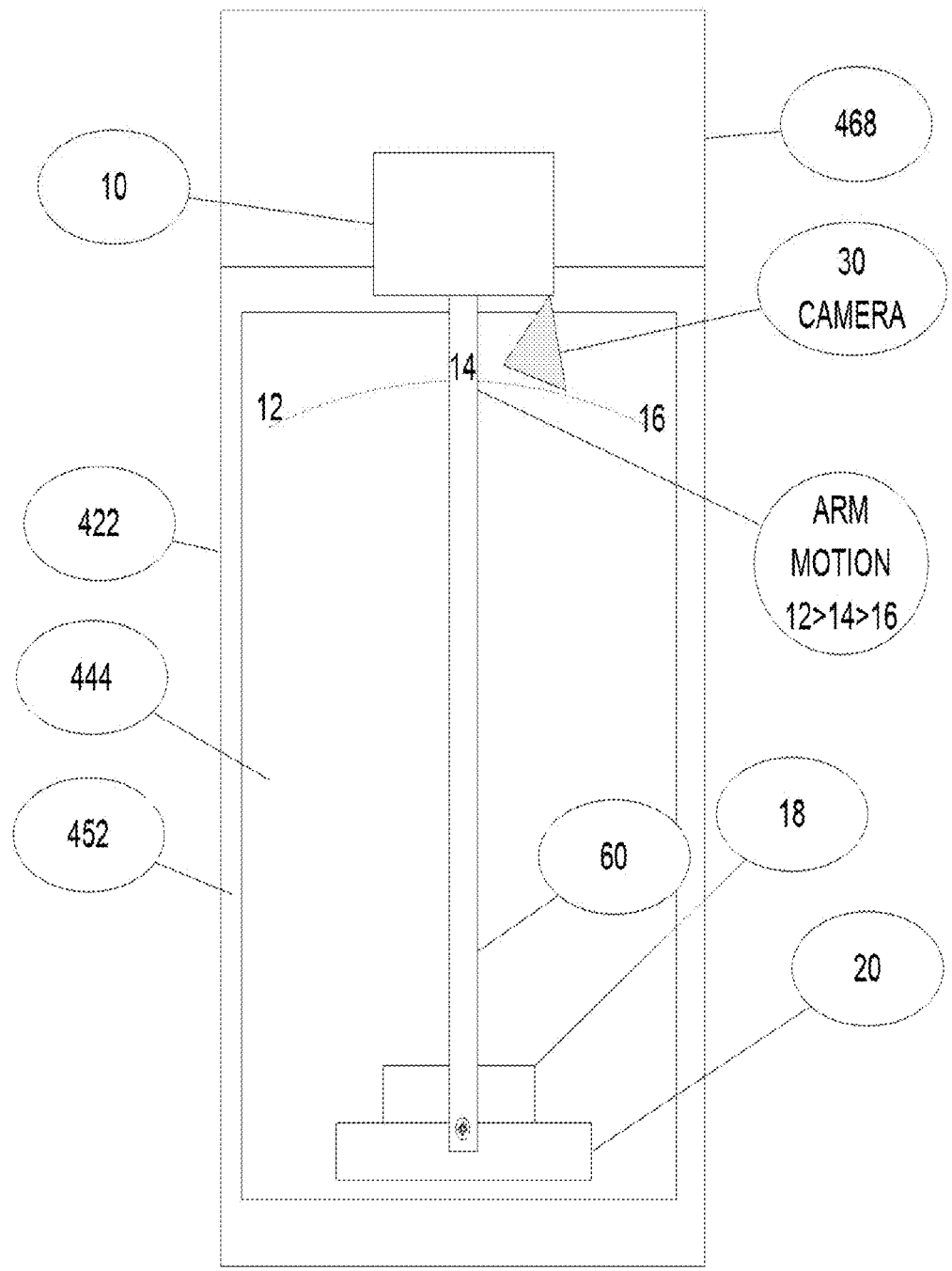
FIG. 5—Displays the sample chamber of the embodiment of FIG. 4 with the swing arm and a detector.
Figure 6:
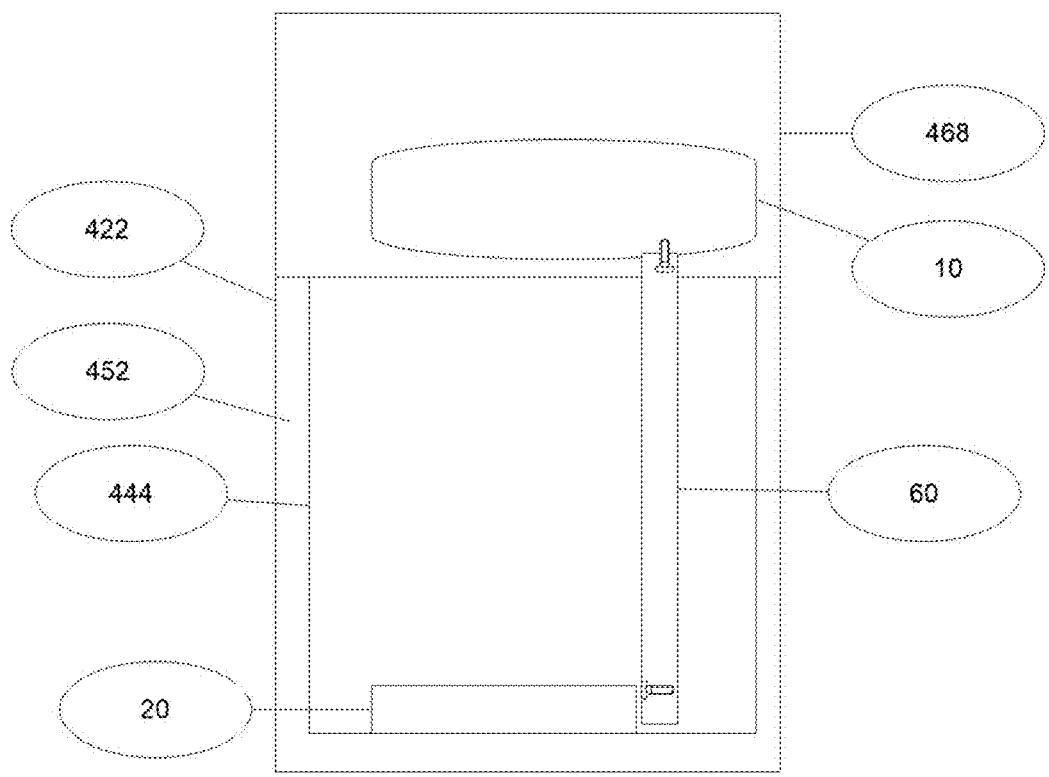
FIG. 6—Displays the lateral view of the X-ray source of the embodiment of FIG. 4 mounted to the top of the swing arm.

In one embodiment, a controller or computer 470 controls the collection of data from the detector 20, controls the swing arm 60 shown in FIGS. 5 & 6, and X-ray source 10. A monitor 472 displays the compiled data and can, for example, be mounted on an articulating arm 474 that is attached to the cabinet 422. The computer 470 receives commands and other input information entered by the operator via a user interface 476, such as a keyboard and mouse for example. In one embodiment, the computer 470 can comprise a touch screen or near touch screen device. Although the aspects of the disclosed embodiments will generally be described with respect to a computer 470, it will be understood that the computer 470 can comprise any suitable controller or computing device. Such computing devices can include, but are not limited to, laptop computers, minicomputers, tablets and pad devices.

The computer 470 can be configured to communicate with the components of the X-ray cabinet system 400 in any suitable manner, including hardwired and wireless communication. In one embodiment, the computer 470 can be configured to communicate over a network, such as a Local Area Network or the Internet.

FIG. 5 shows a front interior view and FIG. 6 shows a lateral interior view of the sample chamber of imaging unit cabinet of FIG. 4. In this embodiment, a sample 18 is placed or otherwise disposed onto the detector 20. Using the computer 470 shown in FIG. 4, the operator enters in the parameters for the scan via the user interface 476, which can be displayed on the monitor 472. As used herein, the term "display" or "monitor" means any type of device adapted to display information, including without limitation CRTs, LCDs, TFTs, plasma displays, LEDs, and fluorescent devices. The computer 470 then sends the appropriate commands to the X-ray source 10 and detector 20 to activate image collection while the swing arm 60 is moving as a result of the servo mechanism disclosed above along a path or arc from position 14 to 12 to 16 (which are shown in FIGS. 1 and 5) or vice versa as described, which in this embodiment are at 345°, 0°, and 15° respectively with 0° at top dead center. At the end of the travel of the swing arm 60 at either position 12 or 16, the computer 470 issues the command to the X-ray source 10 and the detector 20 to cease operating. The individual 2-dimensional (2-D) images which were collected, in this example at 1° increments, are then tabulated in the computer 470 to create the tomosynthetic images. In one embodiment, the operator may select which images of the images of the embodiments of the present disclosure they wish via the user interface 476 as they are being displayed on the monitor 472. In one embodiment, the devices and components of the X-ray cabinet system 400 are suitably communicatively coupled together, including one or more of hard wire connections or wireless connections using a suitable wireless connection and communication transmission protocol, as will generally be understood. The X-ray cabinet system 400 can also be configured to transfer images via USB, CD-ROM, or WIFI.

The dynamic imaging software of the disclosed embodiments reconstructs three-dimensional images (tomosynthesis) from two-dimensional projection images in real-time and on-demand. The software offers the ability to examine any slice depth, tilt the reconstruction plane for multiplanar views and gives higher resolution magnifications.

Figure 7A:
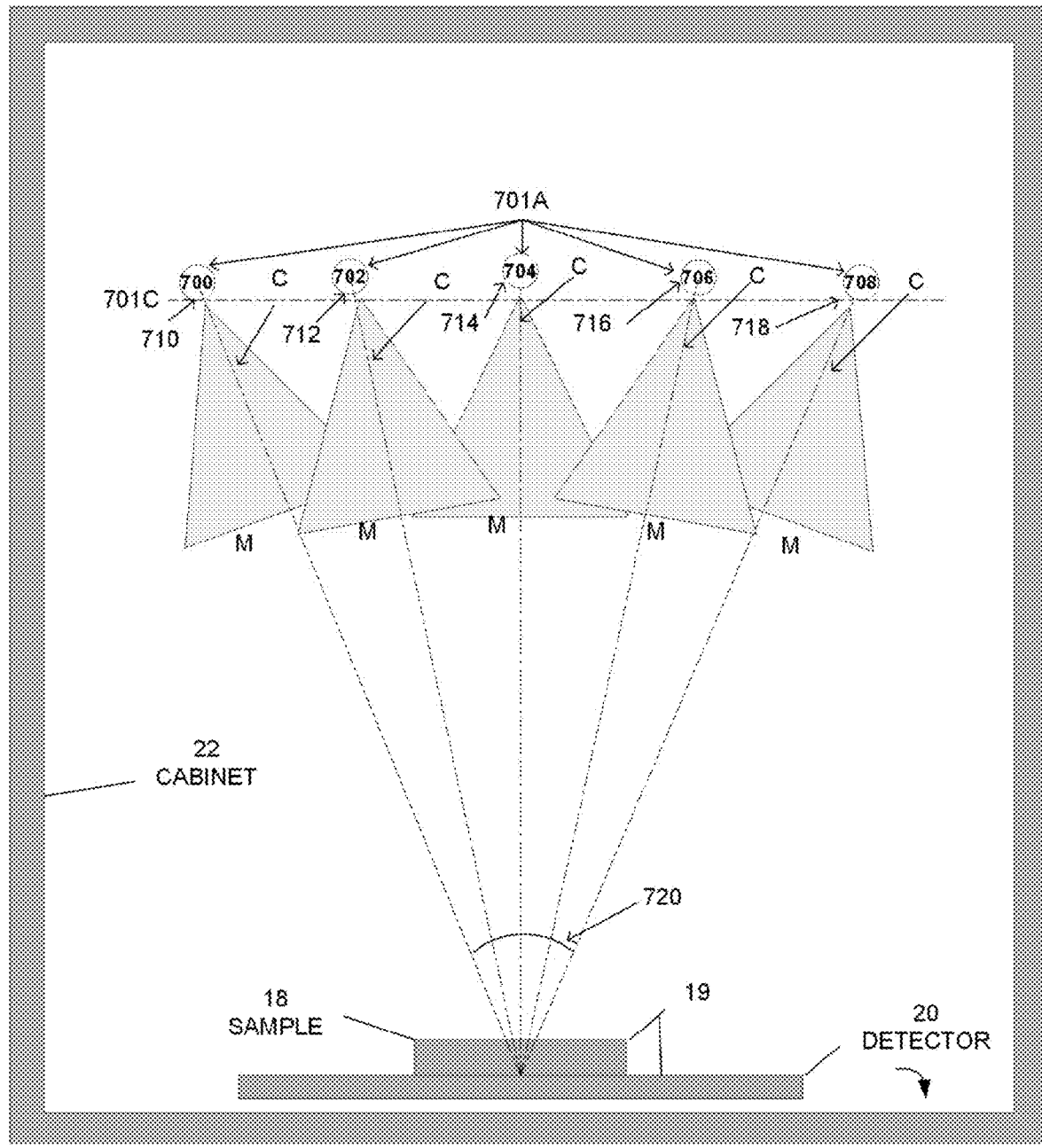
FIG. 7A—Schematically illustrates another embodiment of the present disclosure including a front view of a multitude of fixed X-ray sources, a specimen/sample, and a digital detector, where the X-ray source moves relative to the specimen for imaging the specimen at different angles, in one embodiment of a system incorporating aspects of the present disclosure.
Figure 7B:
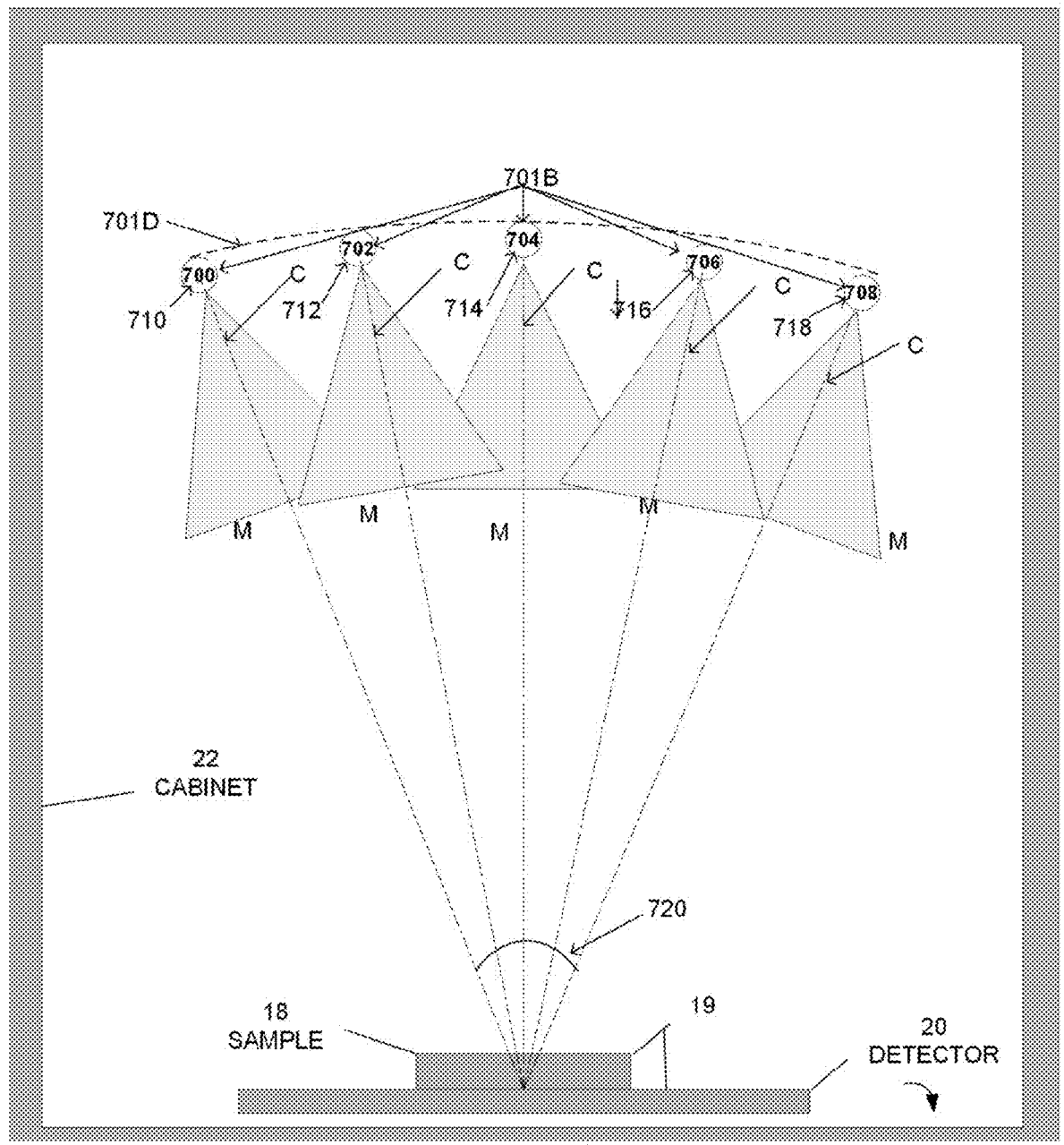
FIG. 7B—Schematically illustrates another embodiment of the present disclosure including a front view of a multitude of fixed X-ray sources, a specimen/sample, and a digital detector, where the X-ray source moves relative to the specimen for imaging the specimen at different angles, in one embodiment of a system incorporating aspects of the present disclosure.

Another embodiment of the present disclosure is illustrated in FIGS. 7A and 7B that operate and include the aspects and features illustrated in the embodiments of FIGS. 1-6 except the embodiments of FIGS. 7A and 7B include an array or plurality of fixed X-ray sources at fixed points, for example, X-ray sources 700, 702, 704, 706, and 708, in place of the travel of X-ray source 10 moving (FIG. 1) swing arm 60 (FIG. 5) servo mechanism. 710, 712, 714, 716, and 718 illustrate exemplary positions of X-ray sources 700, 702, 704, 706, and 708, respectively. An optical camera and NIR system similar to those included in the present disclosure can be incorporated into the embodiments in FIGS. 7A and 7B as they are incorporated into other embodiments of the present disclosure.

The aspects of the embodiments illustrated in FIGS. 7A and 7B include at least one array or plurality of X-ray sources 701A positioned in a linear shaped arrangement along substantially linear axis 701C, as shown in FIG. 7A or at least one array or plurality of X-ray sources 701B positioned in an arc shaped arrangement along arc or curved axis 701D, as shown in FIG. 7B. The reference "C" at each of the X-ray sources 700, 702, 704, 706 and 708 in FIGS. 7A and 7B refers to the point source of the X-ray beam from each X-ray source. The reference "M" refers to the spread or fan of the X-ray beam from each X-ray source.

X-ray sources 700, 702, 704, 706 and 708 can be distributed at positions 710, 712, 714, 716 and 718, respectively, in FIGS. 7A and 7B with the end positions of the array, for example, between the point source "C" line of the beam of 700 at position 710 and the point source "C" line of the beam of 708 at position 718, are separated by an arc 720 of from about 20° to about 50°, preferable about 30°, more preferable about 20° with one X-ray source, for example, the point source "C" line of the beam of 704 at position 714 positioned at about 0°. The other X-ray sources 702 at position 712, and 706 at position 716 can be positioned such that each of those X-ray sources are positioned in between X-ray sources 700 and 708 along linear axis 701C, as shown in FIG. 7A or arc or curved axis 701D, as shown in FIG. 7B, and may be evenly spaced. The following are exemplary positions for the embodiments of FIGS. 7A and 7B can be used. Exemplary Configuration 1—about 350° (reference position 710), about 355° (reference position 712), about 0° (reference position 714), about 5° (reference position 716) and about 10° (reference position 718); Exemplary Configuration 2—about 340° (reference position 710), about 350° (reference position 712), about 0° (reference position 714), about 10° (reference position 716) and about 20° (reference position 718); Exemplary Configuration 3—about 335° (reference position 710), about 347.5° (reference position 712), about 0° (reference position 714), about 12.5° (reference position 716) and about 25° (reference position 718); between approximately 340° (reference position 12) to 0° (reference position 14) to 20° (reference position 16) and or between approximately 335° (reference position 12) to 0° (reference position 14) to 25° (reference position 16).

In another embodiment, X-ray sources 700, 702, 704, 706 and 708 can be positioned at 710, 712, 714, 716 and 718, respectively, in FIGS. 7A and 7B, such that the point source "C" line of the beam of each the X-ray sources at either end of the array, the point source "C" line of the beam of 700 at position 710 and the point source "C" line of the beam of 708 at position 718, are separated by an arc 720 of from about 20° to about 50° arc, preferable about 30°, more preferable about 20°, with one X-ray source the point source "C" line of the beam of 704 at position 714 is positioned at about 0°. The other X-ray sources 702 at position 712, and 706 at position 716 can be positioned such that the point source "C" of the beam of each of those X-ray sources are positioned within arc 720, preferable with the point source "C" line of the beams of X-ray sources 702 at position 712, 704 at position 714 and 706 at position 716 are evenly distributed between the point source "C" line of the beam X-ray sources 700 at position 710 and 708 at position 718. For example, X-ray source 700 can be positioned with a point source "C" line of the beam thereof at about 350°, X-ray source 702 can be positioned with a point source "C" line of the beam thereof at about 355°, X-ray source 704 can be positioned with a point source "C" line of the beam thereof at about 0°, X-ray source 706 can be positioned with a point source "C" line of the beam thereof at about 5° and X-ray source 708 can be positioned with a point source "C" line of the beam thereof at about 10°. For another example, X-ray source 700 can be positioned with a point source "C" line of the beam thereof at about 340°, X-ray source 702 can be positioned with a point source "C" line of the beam thereof at about 350°, X-ray source 704 can be positioned with a point source "C" line of the beam thereof at about 0°, X-ray source 706 can be positioned with a point source "C" line of the beam thereof at about 10° and X-ray source 708 can be positioned with a point source "C" line of the beam thereof at about 20°. For still another example, X-ray source 700 can be positioned with a point source "C" line of the beam thereof at about 335°, X-ray source 702 can be positioned with a point source "C" line of the beam thereof at about 347.5°, X-ray source 704 can be positioned with a point source "C" line of the beam thereof at about 0°, X-ray source 706 can be positioned with a point source "C" line of the beam thereof at about 12.5° and X-ray source 708 can be positioned with a point source "C" line of the beam thereof at about 25°.

The ranges recited herein are intended to be approximate and inclusive of start and endpoints.

The number of X-ray sources in the arrays or pluralities of X-ray sources 701A and 701B can range from a minimum total of at least about 3 to about 11 or more, about 5 to about 11, and in some examples, about 5, about 7, about 9, about 11, and also an odd number of X-ray sources, further including for each of these aforementioned ranges wherein one of the X-ray sources is positioned at about 0° or the point source "C" line of one of the X-ray beams is positioned at about 0°. An alternative embodiment can include arrays or pluralities of X-ray sources 701A and 701B distributed such that the point sources of adjacent X-ray sources in the array or plurality are separated by about 1° to about 5°. As with other embodiments of the present disclosure the X-ray detector 20 is stationary as is the sample 18 and the X-ray detector can include, for example, a flat panel X-ray detector including a flat panel digital X-ray detector. The X-ray cabinet 22, the detector 20, the sample 18 and the specimen platform 19 (which is a protective cover) or another surface of the detector 20 are the same as included in the embodiment of FIG. 1. As with other embodiments of the present disclosure, the isocenter of the image acquisition geometry is located below the sample, on the surface of the detector.

Each X-ray source of the array or plurality (e.g., X-ray sources 700, 702, 704, 706 and 708) can be activated to emit an X-ray beam one at a time so that the detector 20 receives only one image at a time. The sequence of activating the X-ray sources can be random, and may also be, for example, from left to right (e.g., first 700, second 702, third 704, fourth 706 and fifth 708) or right to left (e.g., first 708, second 706, third 704, fourth 702 and fifth 700).

Operation of the embodiments of FIGS. 7A and 7B that is different from what is included in the present disclosure in FIG. 3 includes at 316 the detector 20 capturing images from X-rays emitted from each of the fixed X-ray sources (e.g., X-ray sources 700, 702, 704, 706 and 708) that are included in the array or plurality of X-ray sources and storing the captured image along with the identification of the specific X-ray source (e.g., X-ray sources 700, 702, 704, 706 and 708) from which it originated, using the latter information to identify the position of the X-ray source relative to the sample. The captured images and identification of the specific X-ray source (e.g., X-ray sources 700, 702, 704, 706 and 708) from which each originated are stored 318 and digital tomosynthesis is performed 320. The tomosynthesis image is then displayed 324.

One advantage of having a fixed array of X-ray sources (compared to, for example, having one X-ray source that is moved by, e.g., a motion control mechanism) is the elimination of moving parts needed to move the single X-ray source, the elimination of vibration caused by X-ray source movement during use which could cause blurring or artifacts, the faster acquisition of X-ray images as energizing each of the plurality of X-ray sources need only rely on computer controlled (e.g., computer 470) and don't need to wait until the single X-ray source is moved into position, and a more precise angle resolution because each of the X-ray source in the plurality or array are fixed in position rather than having to rely on a moving X-ray source where its position can be less precise during operation.

The real-time image reconstruction of the present disclosure enables immediate review, higher throughput, and more efficient interventional procedures reducing patient call backs and data storage needs. Multiplanar reconstruction enables reconstruction to any depth, magnification and plane, giving the viewer the greater ability to view and interrogate image data, thereby reducing the likelihood of missing small structures. Built-in filters allow higher in plane resolution and image quality during magnification for greater diagnostic confidence. Software is optimized for performance using GPU Technology.

The reconstruction software used in conjunction with the aspects of the present disclosure provides the users greater flexibility and improved visibility of the image data. It reconstructs images at any depth specified by the user rather than at fixed slice increments. With fixed slice increments, an object located between two reconstructed slices, such as a calcification, is blurred and can be potentially missed. The aspects of the present disclosure provide for positioning the reconstruction plane so that any object is exactly in focus. This includes objects that are oriented at an angle to the detector 20. The aspects of the present disclosure provide for the reconstruction plane to be angled with respect to the detector plane.

Figure 8:
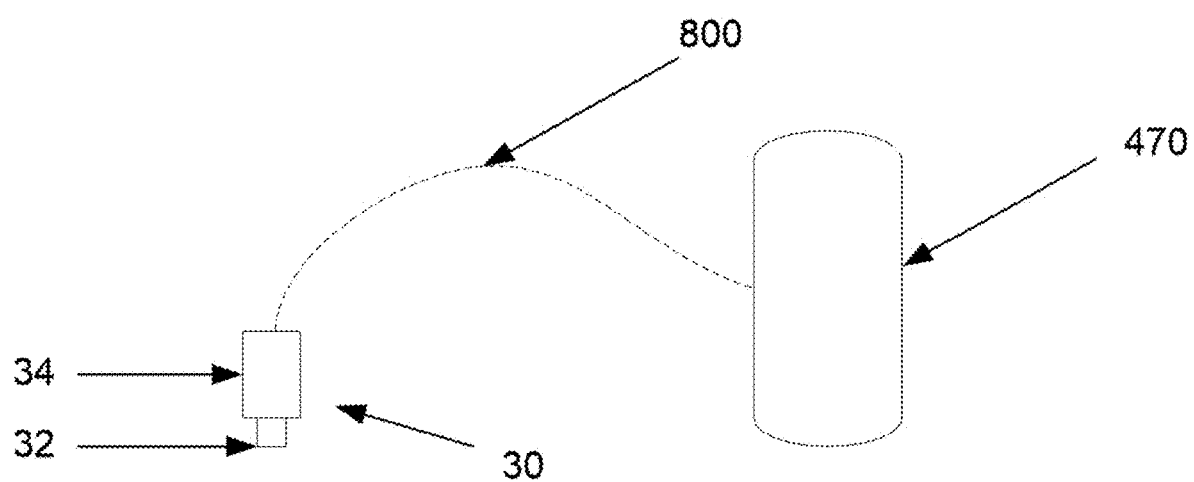
FIG. 8—Displays an interconnection diagram of an HD camera embodiment that may be utilized in aspects of the disclosed embodiments of the present disclosure.
Figure 9:
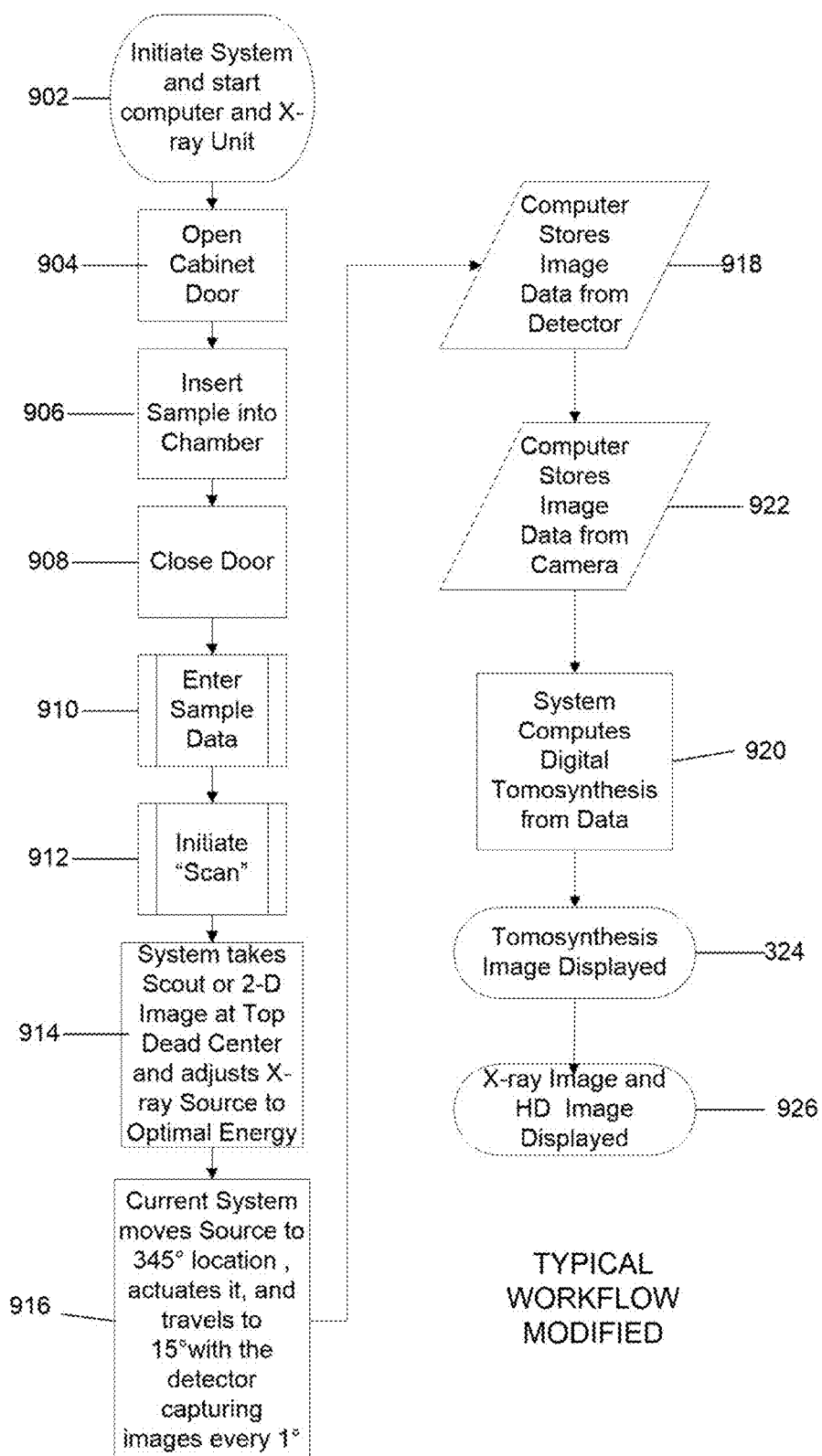
FIG. 9—Displays an exemplary modified workflow/flowchart of an aspect of the disclosed embodiments.

FIGS. 8-10 depict various features of embodiments of the present disclosure, which embodiments are generally directed to a system that can utilize an optical camera or a real-time camera, to capture a visual image of a specimen/sample concurrently or at substantially the same time as the acquisition of an X-ray image. Referring to FIG. 8, there is shown the interconnection of an embodiment of a camera 30 incorporated into a Cabinet X-Ray Unit which connects to and can be controlled by the computer 470 via cable 800 including, for example a USB cable. Other wireless formats for communication between camera 30 and computer 470 can also be used in embodiment of the present disclosure. Camera 30 may include an optical lens assembly 32 through which an optical image passes and is focused upon an electronic light-sensitive sensory array included in the camera body 34. The optical image can then be sent using an electronic signal from the sensory array to the computer 470 via cable 800 or other wireless formats. The optical image as well as a 2-D X-ray image or tomosynthesis image can also be stored in the computer 470 for future examination and viewing, including storage in memory (e.g., RAM) or a disc recording medium (e.g., a hard drive, CD, DVD, etc.)

Camera 30 is included in FIGS. 1, 2 and 5 as well showing embodiments in camera 30, for example, located at position 15 in the cabinet X-ray unit such that it is capable of capturing a visual image of sample 18 in cabinet 22 and X-ray cabinet chamber 28 in FIGS. 1 and 2 and in cabinet 422 and sample chamber 444 in FIG. 5, such that the optical image captured by camera and the X-ray image (2-D X-ray image or tomosynthetic X-ray image) show the sample or specimen at substantially, or in some embodiments at exactly, the same orientation for the optical and X-ray images. In one embodiment, a medical professional or other authorized operator places a specimen/sample into the chamber, closes and secures the door, and presses, for example, the "acquire" command on the system using, for example, a keyboard or touch screen monitor that can be used to enter system commands or other information. In one embodiment, pressing this command can simultaneously or in substantially close proximity in time, the computer commands the optical camera and X-ray source in conjunction with the X-ray detector to capture images from both sources, the latter being an X-ray image or series of images from which tomosynthetic images can be assembled. In another embodiment, as a result of pressing this command, the X-ray source in conjunction with the X-ray detector captures an X-ray image or series of images from which tomosynthetic images can be assembled. The resulting X-ray image or tomosynthetic image can then be displayed at the same time as or separately from a real-time optical image captured through the camera.

In the systems and methods included in this disclosure as well as the embodiments disclosed herein, the resulting X-ray generated and optical camera images can be displayed each alone or together as overlaid, blended or otherwise combined, adjacent, or in a PIP (Picture-in-Picture) format on the monitor 472 (FIG. 4). This, in turn, provides more flexibility for a medical professional, clinician or other user of the system and simplifies the procedure. The separate images from the camera and X-ray detector as well as the tomosynthetic, overlaid, blended or otherwise combined, adjacent, and PIP images can be stored in the computer hard drive on the system 470 or a separate memory device, such as for example, a separate hard drive, flash drive, CD-ROM, DVD, etc. for future analysis. The camera can capture a visible light or other electromagnetic wavelength reflected or emitted by the sample or portions thereof, for example, though the use of fluorescent or other markers using a suitable light source where required. Manual input for operation of the cabinet X-ray unit may be initiated via keyboard or monitor touch screen and the resulting image from both the manual-initiated examination can be displayed on the screen and configured in accordance with one example embodiment of the present disclosure.

FIG. 9 illustrates one embodiment of a modified basic workflow of the cabinet X-ray unit with the addition of the storage of the image data 922 and the combination X-ray image and HD image displayed 926.

As will be generally understood, the system 100 is initiated 902, the X-ray cabinet door 24 opened 904, and the sample 18 placed into 906 the X-ray cabinet chamber 28. As shown in FIG. 2, for example, the sample 18 is positioned on the detector 20 in a suitable manner. The door 24 is closed 908.

The data and information regarding the sample 18, including any other suitable information or settings relevant to the imaging process and procedure, is entered 910 into the computer 470. The scan is initiated 912. The system 100 will take 914 scout or 2-D images at Top Dead Center, which for purposes of this example is position 14 of FIGS. 1 and 2. The X-ray source 10 can then be moved to other positions, such as positions 12 and 16, and the detector 20 can be used to capture 916 images at various increments along the travel path of the X-ray source 10, such as about every 1 degree. An optical image, for example, an HD image, is captured by the camera and stored in the computer 922. The captured images are stored 918 and digital tomosynthesis is performed 920. The tomosynthesis image is then displayed 924. The combination X-ray image and HD image are then displayed 926, the X-ray image can be either the 2-D image from 914 or the tomosynthesis image from 920. Another embodiment of the workflow embodiment illustrated in FIG., 9 can include obtaining a 2-D X-ray image as in 914 without the detector 20 being used to capture 916 images at various increments along the travel path and related steps 920 and 924 related to tomosynthesis FIG. 10A exhibits the HD image of a breast specimen and FIG. 10B exhibits the X-ray image of the specimen showing the actual placement of the markers 1002 and orientation of the specimen as well as placement of the markers 1002 within the breast specimen 1000. Markers 1002 are utilized to delineate the outer boundaries of the suspect area that needs to be excised in the X, Y, and Z directions. The markers may include radioactive seeds, coils, wires, and/or radiopaque/visible items which are implanted before the surgery by an interventional radiologist prior to the surgery and are utilized to denote boundaries of the region of interest.

FIG. 11A shows an X-ray image of a breast specimen, a gray scale X-ray image produced directly from the X-ray source and X-ray detector of the embodiments of the present disclosure, and FIG. 11B shows the image of the X-ray image of FIG. 11A overlaid, blended or otherwise combined with the optical image of the specimen 1104 showing the actual placement of the markers 1102 and orientation of the specimen as well as placement of the markers 1102 within the breast specimen 1100. Markers 1102 are utilized to delineate the outer boundaries of the suspect area that needs to be excised in the X, Y, and Z directions. The markers may include radioactive seeds, coils, wires, and/or radiopaque/visible items which are implanted before the surgery by an interventional radiologist prior to the surgery and are utilized to denote boundaries of the region of interest.

Figure 11C:
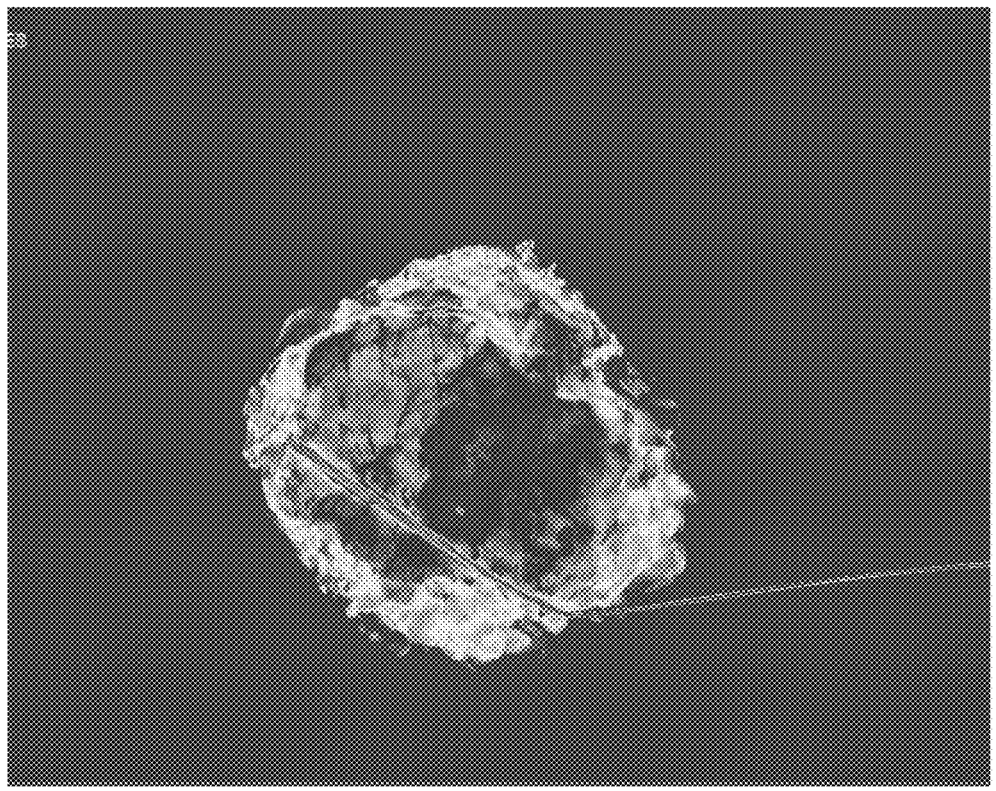
FIG. 11C—Displays a colorized radiographic image according to exemplary embodiments of the present disclosure.

FIG. 11C shows the original grayscale X-ray image from FIG. 11A after the computer 470 has analyzed the different densities or ranges of densities and has assigned a color to them. Specifically, with FIG. 11C, it is colorized with various shades of red being the densest areas going to white being the least dense. Blue and Purple are displayed in FIG. 11C in varying intensities to convey to the medical professional viewing the image the differences of densities of the specimen shown in the image.

For exemplary descriptive purposes, in a normal X-ray or tomosynthetic image (i.e., before the densities of the different area of the specimen are determined and an image produced therefrom), there can be five different densities that can be useful to determine the nature of an abnormality (e.g., air, fat, soft tissue, bone and metal). If there is an unexpected increase or decrease in the density of a known anatomical structure then this may help determine the tissue structure of the abnormality. Low density material such as air is represented as black on the normal X-ray or radiograph image. Very dense material such as metal or contrast material is represented as white. Bodily tissues are varying degrees of gray, depending on density, and thickness. Utilizing artificial intelligence and neural networks, the algorithm of embodiments of the present disclosure can take the varying degrees of gray of a normal X-ray image and interpolates them in a color palate or gray scale where the different colors or shades of gray indicate different densities or a range of densities of areas of the specimen. Changes in color can be more easily perceived than changes in shades of gray of the initial X-ray image and therefore this procedure makes the interpretation and understanding of the image easier for the medical professional. During colorization, for example, the algorithm replaces a scalar value representing pixel's intensity with a vector in a given color space. Since the mapping between intensity and color has no inherently correct solution, human interaction and external information usually plays a large role in evaluating the original X-ray image.

One embodiment of the present disclosure utilizes a controller or computer of embodiments of the present disclosure, for example a controller or computer 470 in FIG. 4, to control, manage, manipulate and analyze the image data obtained by the cabinet X-ray system or unit and other embodiments of the present disclosure in order to analyze the different densities of a specimen and assigning a color to each of those densities. One embodiment for obtaining and analyzing the different densities of a specimen and assigning a color to each of those densities includes beaming X-rays through tissue of a specimen and measuring their magnitude (i.e., intensity) after they have passed through the specimen utilizing an X-ray detector, for example, X-ray detector 20, the X-ray detector including, for example, a plurality of pixels including a two-dimensional array of pixels used to detect incoming X-rays emitted from an X-ray source, for example, X-ray source 10 of embodiments of the present disclosure. Some of the pixels will detect X-rays. Since denser materials like bone will attenuate (weaken the energy) the X-rays more than soft tissue does, their shape becomes clear as a flat, monochrome image in the colorized image embodiments of the present disclosure. The detector can measure the attenuation of specific wavelengths of the X-rays as they pass through different materials. In normal X-ray images, the above is visualized utilizing gray scale. One embodiment for generating the image where the darkness of the gray scale is for more dense areas or different colors denoting the density of different areas, uses an algorithm to record the magnitude (i.e., intensity) of each pixel of the detector that is received by the detector and based on the magnitude (i.e., intensity) being emitted from the X-ray source, for example, X-ray source 10, determines the difference in magnitude between the source and what is received by the detector. An algorithm, different or incorporated into other algorithms disclosed herein, can use that information on the difference from each pixel of the detector to produce an image whereby the quantity of the difference in magnitude (i.e., intensity) at each pixel and a specific color (or shades of a color) or gray scale level is assigned to each such difference or range of differences in magnitude (i.e., intensity) for all the pixels and an image is then displayed of the specimen in those colors, shades of color or gray scale showing the different densities or range of densities of parts of the specimen. For example, after running the data through the specific algorithms, a color image can generated that shows muscle, bone, water, fat, disease markers so that their presence in the specimen can then be determined. That means two objects of similar density but different materials can be distinguished.

Separate image layers for each material, for example, one layer containing only bone, one containing only fat, etc. of the original X-ray image can be assigned a color (or color range) or gray scale level for each material of the specimen. Any color can be chosen, but in one embodiment, colors can be chosen that look similar to what one would expect to see in the specimen itself. Once the colors (or color range) or gray scale for the different densities or range of densities are chosen, the different colors (or color range) or gray scale for those areas of the specimen are combined to produce a single color or gray scale image. Such images can also be adjusted to edit out one or more specific density amounts or range of density amounts, thus, only showing in an image, those densities or range of densities that a medical professional desires to examine and have in the image.

Gain on a camera may represent a conversion factor from electrons (e-) into digital counts, or Analog-Digital Units (ADUs). Gain may be expressed as the number of electrons that get converted into a digital number, or electrons per ADU (e-/ADU). Cabinet X-ray systems or units of the present disclosure can operate by analyzing the ADU units that are the formation of all photographs whether they be radiographs or photographs. Such embodiments can minutely compare the differences between neighboring pixels in terms of magnitude and succinctly assigns a color, shade of color or gray scale level to each density or range of densities after assigning a color or gray scale for full black and one for full white.

A radiographic image is composed of a 'map' of X-rays that have either passed freely through the specimen or have been variably attenuated (absorbed or scattered) by anatomical structures. The denser the tissue, the more X-rays are attenuated. For example, X-rays are attenuated more by bone than by lung tissue. Contrast within the overall image depends on differences in both the density of structures in the body and the thickness of those structures. The greater the difference in either density or thickness of two adjacent structures leads to greater contrast between those structures within the image.

Another embodiment of the cabinet X-ray systems or units of the present disclosure can distinguish different material of the specimen by training or including an algorithm to analyze the system imaging the specimen using the same technique, kVp and mA (the mA (tube current and exposure time product) and filtration, kVp (tube voltage), two settings that can be adjusted on X-ray system to control the image quality and patient dose. The algorithm would need to be calibrated and it would record the ADU unit for each density/material in the specimen and utilizing a table or other list in memory of information on the densities of different material, discern the different materials making up the specimen.

Another embodiment of the present disclosure can use the difference in X-ray magnitude from each pixel that indicates the density of area of the specimen in a 2-D X-ray and then using that difference (e.g., either from the difference data directly or from 2-D density X-ray images formed using that data) from multiple such 2-D X-ray images of the same specimen area to generate a colorized tomosynthetic image denoting density in that tomosynthetic image.

The detailed images of the embodiments of the present disclosure can be viewed in real-time and/or saved for future examination in various formats in the main computer 470 and then may be transmitted via USB, Ethernet, Wi-Fi, etc. in various formats that may include DICOM, .tiff. or .jpeg, non-inclusive.

Figure 12:
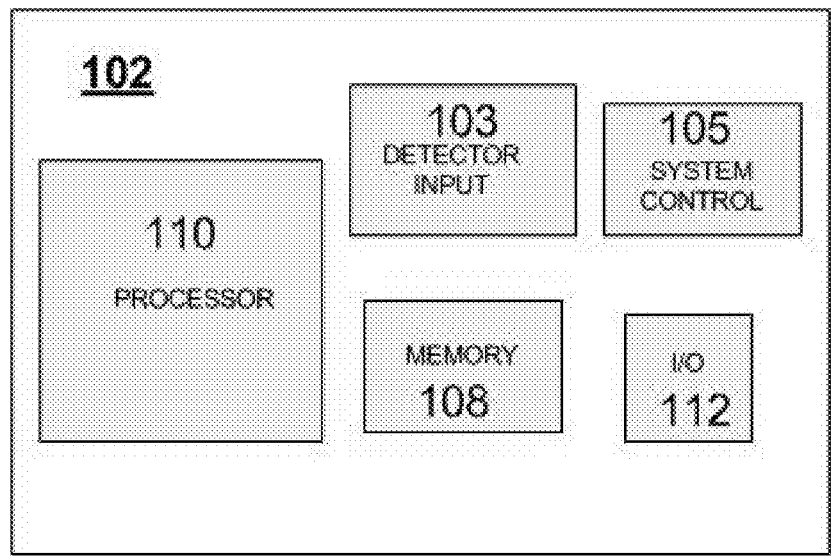
FIG. 12—Displays exemplary computer components of embodiments of the present disclosure.

One embodiment of the cabinet X-ray system or unit of the present disclosure includes a controller or computer, for example a controller or computer 470 in FIG. 4 that includes a processing unit 102 as shown in FIG. 12, a digital detector 103 for collecting an X-ray image of, for example, a breast specimen radiogram, the X-ray radiogram from a tomosynthesis specimen radiographic system as well as previous figures and disclosure included above and entered at an input 112 to the cabinet X-ray system or unit embodiments of the present disclosure. The processing unit 102 generally includes elements necessary for performing image processing including parallel processing steps of embodiments of the present disclosure. The tomosynthesis specimen radiogram may be one of a plurality of such radiograms that can be used to produce tomosynthetic images. The colorizing of X-ray images or tomosynthetic images to indicate density or a range of densities is another use of the processing unit. In particular, the processing unit 102 includes elements such as a central control unit 105, a memory 108, a parallel processing unit 110, and I/O (input/output) unit 112. The central control unit 105 performs the commands to manipulate the data. Memory 108 performs the temporary storage and manipulation of the data as well as storage of algorithms and other software used by the cabinet X-ray system or unit or other embodiments of the present disclosure in performing aspects of the embodiments, methods and systems included herein. Parallel processing unit 110 performs and allows simultaneous calculating, and notation of all images as well as management and manipulation of the data utilizing algorithms and other software used by the cabinet X-ray system or unit or other embodiments of the present disclosure in performing aspects of the embodiments, methods and systems included herein. I/O (input/output) unit 112 performs control of the input data and the resulting output/display. It is to be appreciated that the parallel processing unit 110 shown in FIG. 12 may be replaced by a single processor without departing from the scope of the preferred embodiments. It is to be appreciated that in addition to the image analysis and manipulation algorithms disclosed herein, processing unit 102 is capable of performing a multiplicity of other image processing algorithms either serially or in parallel therewith.

Display or monitor 472 (FIG. 4) is for conveniently viewing both images of embodiments of the present disclosure and the output of the processing unit 102 thereon. Display or monitor 472 may also include a user interface as user interface 476 exemplified in the embodiment of FIG. 4, such as a keyboard and mouse for example. In one embodiment, Display or monitor 472 can comprise a touch screen or near touch screen device separately or integrated as part thereof. Display or monitor 472 may be, for example, an LCD screen. As used herein, the term "display" or "monitor" means any type of device adapted to display information, including without limitation CRTs, LCDs, TFTs, plasma displays, LEDs, and fluorescent devices. Display or monitor 472 typically shows any of the images included in the embodiments of the present disclosure.

Figure 13:
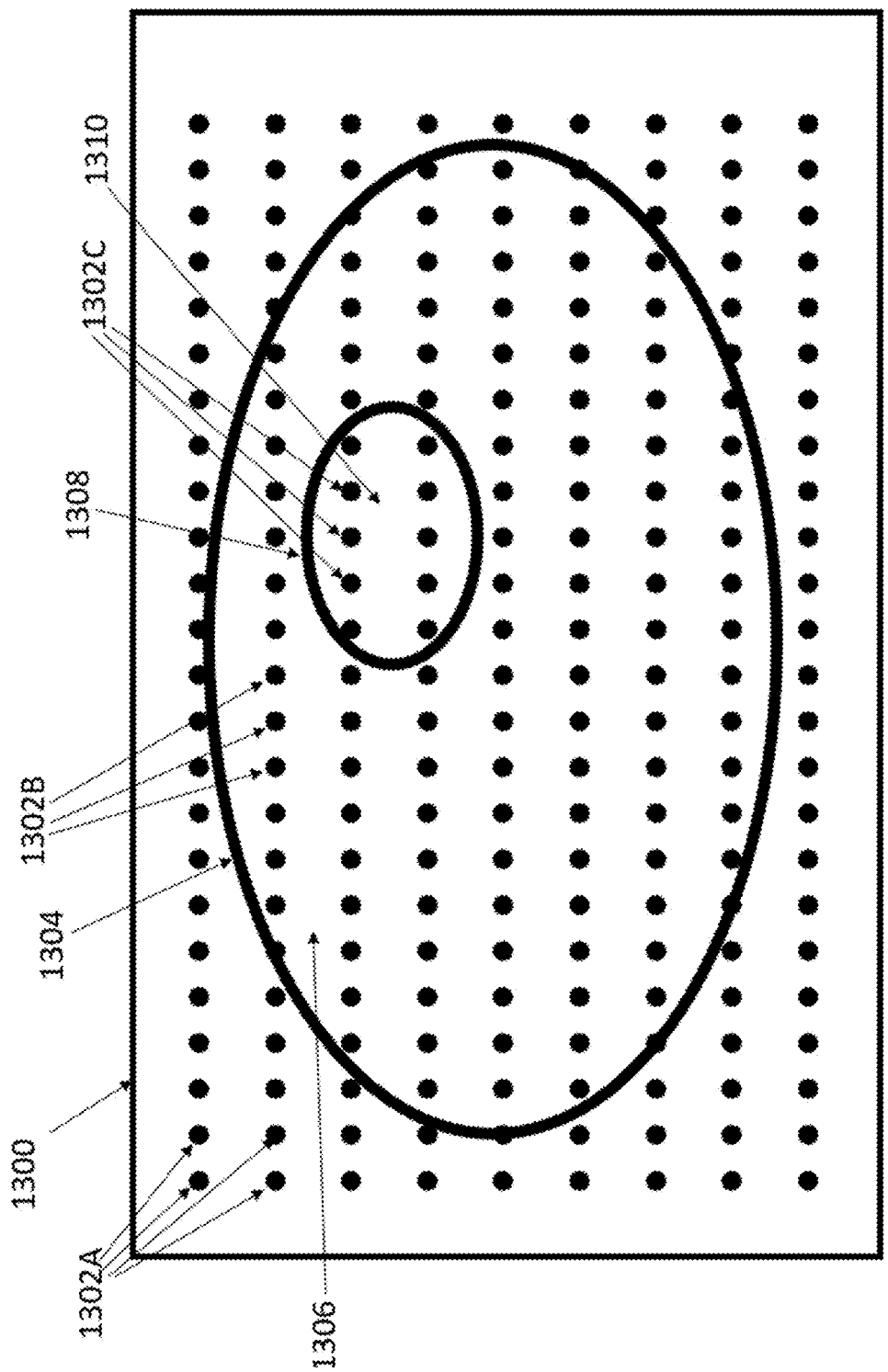
FIG. 13—Illustrates an embodiment of the present disclosure including a top view of an X-ray detector with a specimen thereon.

Embodiments of the present disclosure can be illustrated in FIG. 13 that includes the top view of an X-ray detector 1300 with pixels 1302A, 1302B and 1302C and resting thereon (either directly or indirectly, e.g., a cover) a specimen 1304. A side view of the detector and specimen is similar to what is illustrated in FIGS. 1, 2 and 5. When both X-ray detector 1300 and a specimen 1304 are exposed to an X-ray source or X-ray sources, pixels 1302A, 1302B and 1302C detect the magnitude (i.e., intensity) X-rays as described herein. Specimen 1304 includes as part thereof an area 1306 having one density and within area 1306 another region 1308 with an area 1310 having a different density. Pixels 1302A will detect the incoming X-rays unaffected (e.g., unattenuated). Pixels 1302B will detect the incoming X-rays effected (e.g., attenuated) by the density of area 1306. Pixels 1302C will detect the incoming X-rays effected (e.g., attenuated) by the density of area 1308.

The X-ray and tomosynthetic images including colors (or color range) or gray scale for the different densities or range of densities (the colorized or gray scale density images) and optical images of the same specimen may be displayed where one or the images is in real-time or from being stored in memory on a monitor or display of, for example, of embodiments of the present disclosure, either overlaid onto one another or as a Picture-In-a-Picture (PIP), including at least one of the colorized or gray scale density images with the optical image.

In one embodiment, non-transitory machine-readable instructions being executed by one or more processors of the computer 470 includes the image processing of embodiments of the present disclosure including, for example, creating the colorized or gray scale density images of the present disclosure.

Another embodiment includes superimposition of the overlaid colorized or gray scale density images and optical images of the present disclosure either or both in real-time or from being stored to form a superimposed image. An image blender can be used to perform the superimposition of the images and form one or more superimposed images upon which superimposition can be performed. Superimposition and the combination of two images allows for an adjustment of the degree of opacity and, as a result, the degree of transparency of at least one of the two images, for example, the top image (e.g., one of the colorized or gray scale density images or an optical image, in some embodiments one or both in real time) that is displayed on top of the lower image (e.g., the other one of the colorized or gray scale density images or an optical image, in some embodiments one or both in real time) so that to the viewer, the top image is positioned between the lower image and the viewer's eye and the lower image can be viewed through the top image. With superimposition and the adjustment thereof, the greater the opacity of the top image, the lesser the detail shown of the lower image and lesser the opacity of the top image, the greater the detail shown of the lower image. Each of the images as part of the superimposition image adjustment may be also adjusted utilizing display levelling or brightness and contrast to accentuate or visualize the fiduciary item or structure.

In one embodiment, non-transitory machine-readable instructions being executed by one or more processors of the computer 470 includes the image blender that receives the images and performs superimposition to form a blended image. The computer 470 receives commands to perform the superimposition process and change the first superimposed image to the degree of opacity entered by the operator via, for example, a user interface 476, such as a keyboard, mouse, a touch screen or near touch screen device. Superimposition can be adjusted by the operator using an adjustment device connected to the computer 470 to provide input thereto so that the user can adjust the opacity. Examples of adjustment devices can include a slide bar (e.g., mechanical or virtual on a screen) or other suitable adjustment devices (e.g., a mechanical knob) or by inputting value using the user interface 476. The superimposition scale can be indicated numerically using, for example, a numerical scale or using scale endpoints with no opacity of an image (e.g. the top image) at one end to complete opacity of an image (e.g. the top image) at the other end.

The image blender can control the superimposition process and can receive images in real-time images, stored images or a combination of both. The superimposed image can be viewed on a suitable display or monitor 472 (FIG. 4). Single or multiple superimposed images at various levels of opacity can also be viewed on the display or stored in in the computer hard drive on the system 470 or a separate memory device, such as for example, a separate hard drive, flash drive, CD-ROM, DVD, etc. for future analysis.

Another embodiment can include the image blender aligning the optical image and the colorized or gray scale density images for superimposition. The alignment of the images can include, for example, taking the lower image as background layer and placing the top image on top of the lower image. The image blender can also move and zoom the top image to align it with lower image according to a calibration file included in the image blender (The location and zoom factor of top image layer can be calibrated in prior to the alignment). The user can then adjust to change the opacity of top layer using, for example, a slide bar including, for example, a horizontal slider.

Another embodiment of the present disclosure is a cabinet X-ray and optical camera system, wherein the method and system to selectively distinguish different densities of the X-ray image may produce a colorized image of the X-ray image.

Another embodiment of the present disclosure is a cabinet X-ray and optical camera system for obtaining X-ray images, projection X-ray images, reconstructed tomosynthetic X-ray images and optical images of a specimen, the system including a cabinet defining an interior chamber and an equipment enclosure; a display; an X-ray system (including an X-ray source positioned in the interior chamber; an X-ray detector positioned in the interior chamber; a specimen platform positioned in the interior chamber and which is a protective cover of and in physical contact with the X-ray detector; and a motion control mechanism positioned in the interior chamber and configured for moving the X-ray source to or along a plurality of positions within the interior chamber relative to the specimen disposed on the specimen platform); an optical camera positioned in the interior chamber configured to capture an optical image of the specimen; and a controller positioned in the equipment enclosure. The controller is configured to: selectively energize the X-ray source to emit X-rays through the specimen to the X-ray detector at selected positions of the X-ray source relative to the specimen such that the isocenter of the emitted X-rays at the selected positions is located at a surface of the X-ray detector; control the X-ray detector to collect projection X-ray images of the specimen when the X-ray source is energized at the selected positions, wherein one of the projection X-ray images is a two-dimensional X-ray image taken at standard imaging angle of approximately 0°; create a tomosynthetic X-ray image reconstructed from a collection of projection X-ray images; process the collection of the projection X-ray images in the controller into one or more reconstructed tomosynthetic X-ray images representing a volume of the specimen and relating to one or more image planes that are selectively the same or different from that of the two-dimensional X-ray image; control the optical camera to capture and collect the optical image of the specimen; and selectively display at least one of the two-dimensional X-ray image, the one or more reconstructed tomosynthetic X-ray images either in grayscale or in color and the optical image on the display.

Another embodiment of the present disclosure is a method for obtaining an X-ray image and an optical image of a specimen in a cabinet X-ray and optical image system, processing and displaying the X-ray image either in grayscale or in color and optical image of the specimen. The cabinet X-ray and optical image system includes a cabinet defining an interior chamber; a display; an X-ray system (including an X-ray source; an X-ray detector; and a specimen platform); an optical camera configured to capture an optical image of the specimen; and a controller. The controller is configured to selectively energize the X-ray source to emit X-rays through the specimen to the X-ray detector; control the X-ray detector to collect a projection X-ray image of the specimen when the X-ray source is energized; selectively display the X-ray image on the display; control the optical camera to capture and collect the optical image of the specimen; and selectively display the optical image on the display. The method includes controlling the X-ray detector to collect an X-ray image of the specimen when the X-ray source is energized; controlling the optical camera to capture and collect the optical image of the specimen; and selectively displaying at least one of the X-ray image either in grayscale or color format and the optical image on the display.

Another embodiment of the present disclosure is a method, further comprising displaying the X-ray image either in grayscale or color and the optical image X-ray simultaneously side-by-side or in a picture-in-a-picture format.

Another embodiment of the present disclosure is a method further comprising displaying the X-ray image either in grayscale or color and the X-ray/optical image on the display overlaid/blended. Another embodiment of the present disclosure is a method, wherein the X-ray system further includes the specimen platform having a protective cover of and in physical contact with the X-ray detector; a motion control mechanism configured for moving the X-ray source to or along a plurality of positions within the interior chamber relative to the specimen disposed on the specimen platform; and a controller further configured to selectively energize the X-ray source to emit X-rays through the specimen to the X-ray detector at selected positions of the X-ray source relative to the specimen such that the isocenter of the emitted X-rays at the selected positions is located at a surface of the X-ray detector; control the X-ray detector to collect projection X-ray images of the specimen when the X-ray source is energized at the selected positions, wherein one of the projection X-ray images is a two-dimensional X-ray image taken at standard imaging angle of approximately 0°; create a tomosynthetic X-ray image reconstructed from a collection of projection X-ray images; process the collection of the projection X-ray images in the controller into one or more reconstructed tomosynthetic X-ray images representing a volume of the specimen and relating to one or more image planes that are selectively the same or different from that of the two-dimensional X-ray image; and selectively display the two-dimensional X-ray image and the one or more reconstructed tomosynthetic X-ray images, and the method further includes controlling the X-ray detector to collect projection X-ray images of the specimen when the X-ray source is energized at the selected positions such that the isocenter of the emitted X-rays at the selected positions is located at a surface of the X-ray detector, wherein one of the projection X-ray images is a two-dimensional X-ray image taken at standard imaging angle of approximately 0°; creating a tomosynthetic X-ray image reconstructed from a collection of projection X-ray images; processing the collection of the projection X-ray images in the controller into one or more reconstructed tomosynthetic X-ray images representing a volume of the specimen and relating to one or more image planes that are selectively the same or different from that of the two-dimensional X-ray image; and selectively displaying at least one of the one or more reconstructed tomosynthetic X-ray images either in grayscale or color on the display.

Another embodiment of the present disclosure is a method, further comprising displaying the X-ray image either in grayscale or colorized format or the one or more reconstructed tomosynthetic X-ray images in grayscale or colorized format and the optical image simultaneously side-by-side or picture-in-a-picture.

Another embodiment of the present disclosure is a method, further comprising displaying the X-ray image or the one or more reconstructed tomosynthetic X-ray images either in grayscale or colorized and the optical image on the display overlaid/blended.

Figure 14:
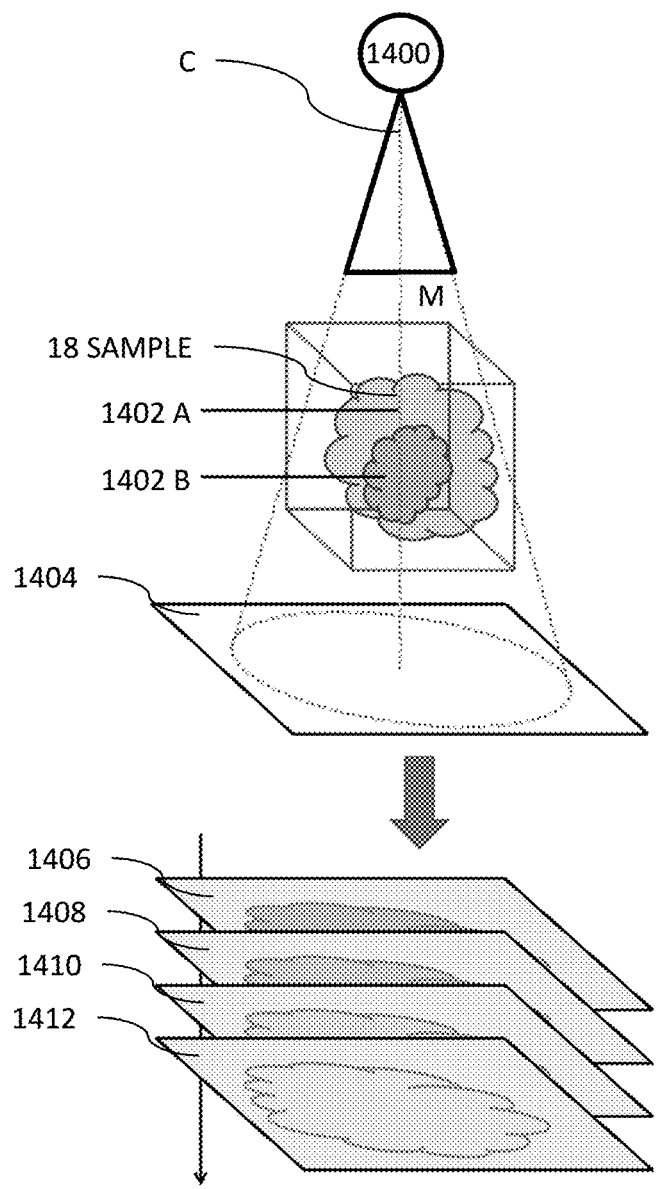
FIG. 14—Illustrates an embodiment utilizing photon-counting for collecting an X-ray image of the specimen.

FIG. 14 illustrates an embodiment utilizing photon-counting for collecting the X-ray image of the specimen. A multi-spectral X-ray source 1400 may project a multi-spectral waveform through the sample 18, having different areas with different densities 1402A, 14028, which is captured by a photon counting detector 1404. The reference "C"

refers to the point source of the X-ray beam and the reference "M" refers to the spread or fan of the X-ray beam.

The resulting compilation of the photon count or intensity of photons impinging on the photon counting detector 1404, as related to the differing densities of the sample 18 may be exhibited by 1406, 1408, 1410, 1412, where pixels of the photon counting detector 1404 are energized at different levels by one or more of different numbers of photons, or an intensity of photons, impinging on the pixels. For example, 1406 may represent outputs of pixels of the detector that may be energized at a higher level from the multi-spectral waveform passing through the least dense portions of the sample 18, 1408 may represent outputs of pixels of the detector that may be energized at a level lower than the pixels in 1406 from the multi-spectral waveform passing through more dense portions of the sample 18, 1410 may represent outputs of pixels of the detector that may be energized at a level lower than the pixels in 1408 from the multi-spectral waveform passing through even more dense portions of the sample 18, and 1412 may represent outputs of pixels that may be energized at an even lower level than the pixels in 1410 from the multi-spectral waveform passing through the most dense portions of the sample 18. The photon counting detector 1404 may be configured to output digital or analog signals or data corresponding to the amount of photons impinging on pixels of the detector 1400, and may also be configured to output digital or analog signals or data corresponding to the intensity of photons impinging on pixels of the detector 1400. The photon counting detector 1404 may further be configured to selectively detect a set of predetermined energy thresholds in order to capture different parts of the X-ray spectrum. Difference in densities detected may change as different predetermined energy thresholds are selected.

It should be understood that the photon counting detector 1400 may be utilized with any of the embodiments disclosed herein.

Varying degrees of gray of the X-ray image resulting from the photon counting pixel outputs may be interpolated in a color palate or gray scale where the different colors or shades of gray indicate different densities or a range of densities of areas of the specimen. A scalar value representing a pixel's intensity may be converted to a vector in a given color space. As disclosed above, the controller or computer 470 in FIG. 4 may be utilized to control, manage, manipulate and analyze image data obtained by the photon counting detector 1400 in order to analyze the different densities of a specimen and assign a color to each of those densities. As a result, a color image may be generated that shows muscle, bone, water, fat, disease markers, and other objects so that their presence in the specimen can then be determined.

As further disclosed above, separate image layers for each material, for example, one layer containing only bone, one containing only fat, etc. of the X-ray image can be assigned a color (or color range) or gray scale level for each material of the specimen. Once the colors (or color range) or gray scale for the different densities or range of densities are chosen, the different colors (or color range) or gray scale for those areas of the specimen may be combined to produce a single color or gray scale image, and the images may be adjusted to show specific density amounts or ranges of density amounts. Furthermore, the image blender of the computer 470 may operate to superimpose, change the opacity, align, or otherwise process the colorized images and the images from the camera.

Figure 15A:
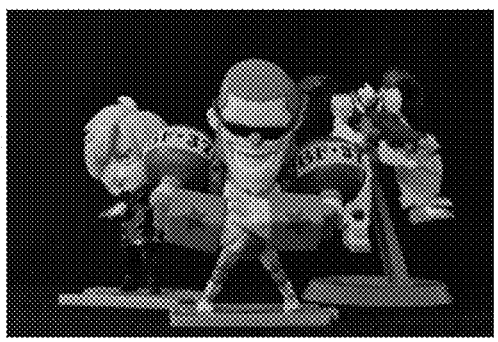
FIGS. 15A-15C—Illustrate three phases of an image captured using the detection techniques disclosed herein.
Figure 15B:
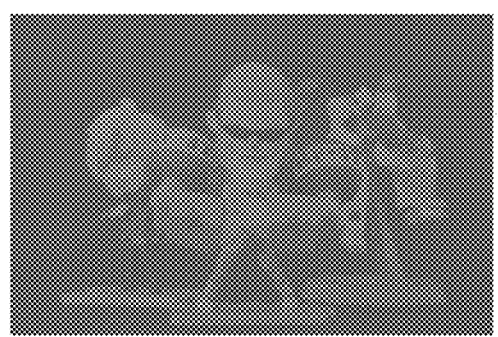
Figure 15C:
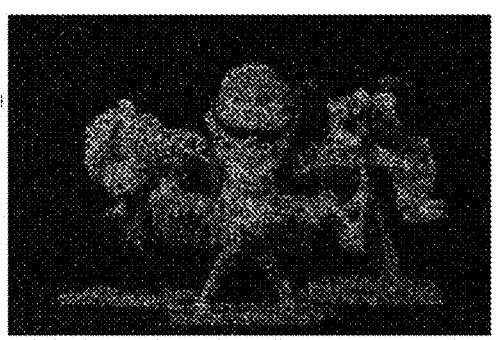

FIGS. 15A-15C, illustrate three phases of an image captured using the detection techniques disclosed herein. FIG. 15A depicts an HD image 1502 captured by the camera 30, FIG. 15B shows an X-ray image 1504 captured by an energy integrating detector, and FIG. 15C shows a pixilated photon-counted image 1504 captured by a photon counting detector.

Figure 16A:
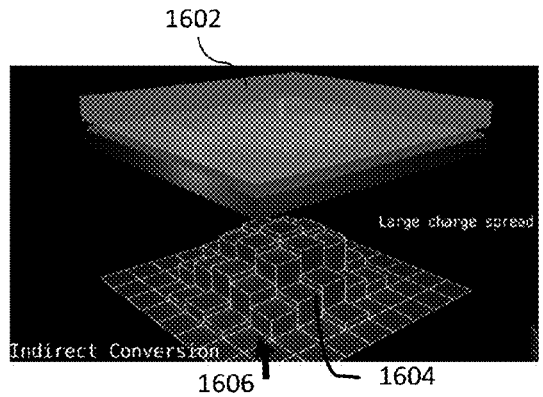
FIGS. 16A, 16B, 17A, 17B, and 17C—Illustrate different detector techniques for converting X-rays to electrical signals and resulting images.
Figure 16B:
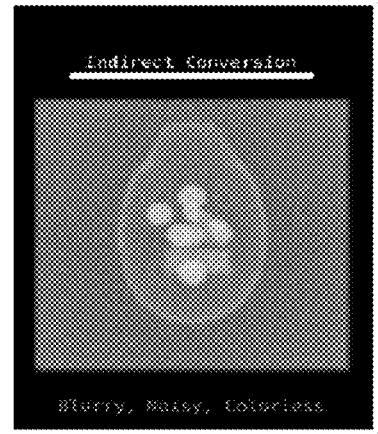

X-ray detectors may utilize different techniques for converting X-rays to electrical signals. FIG. 16A shows an illustration demonstrating an indirect conversion technique where X-rays may impinge on a material 1602 that converts the X-rays to light which then impinges on pixels 1604 of an energy integrating detector. As a result, the light may disperse across a number of pixels resulting in a blurry, noisy image as shown in FIG. 16B.

Figure 17A:
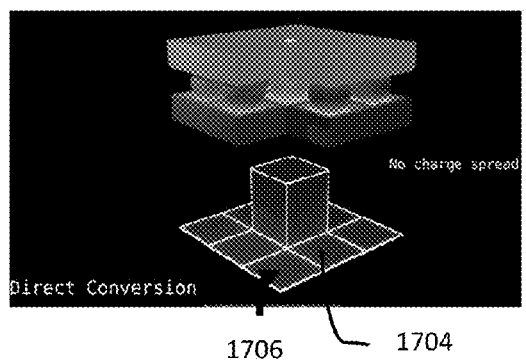
Figure 17B:
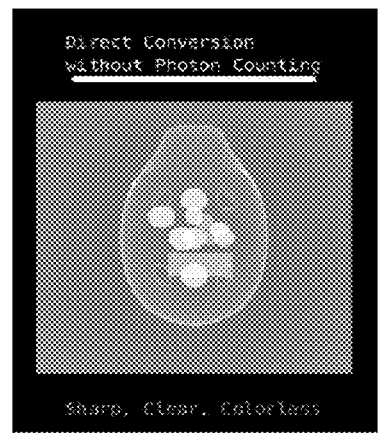
Figure 17C:
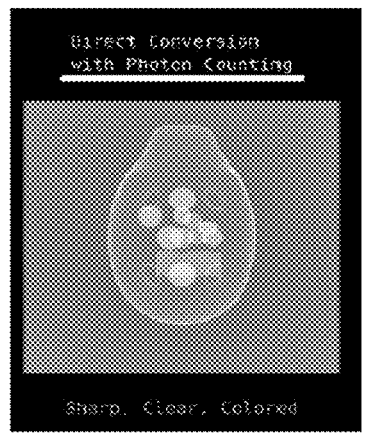

FIG. 17A illustrates a direct conversion technique where X-rays impinge directly onto pixels 1704 of an energy integrating detector 1706, resulting significantly less dispersion across the pixels and a significantly sharper, clearer image as shown in FIG. 17B. FIG. 17C shows a color image with more information, and higher resolution achieved using the photon counting detector 1400 and the colorizing techniques described herein.

Figure 18A:
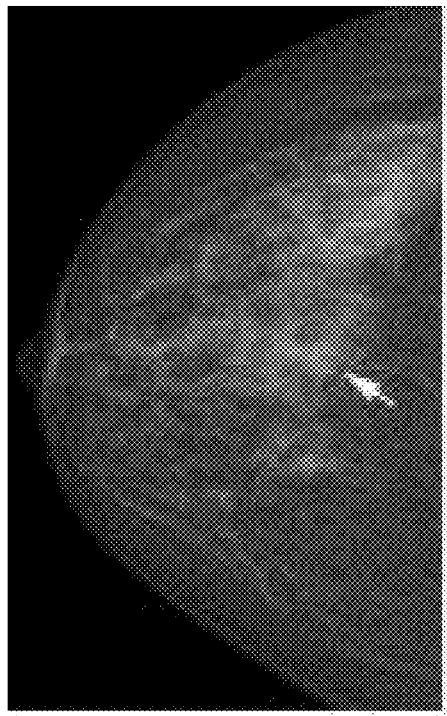
FIGS. 18A, 18B, and 18C—Illustrate two-view screening mammograms obtained with a direct radiography photon-counting system.
Figure 18B:
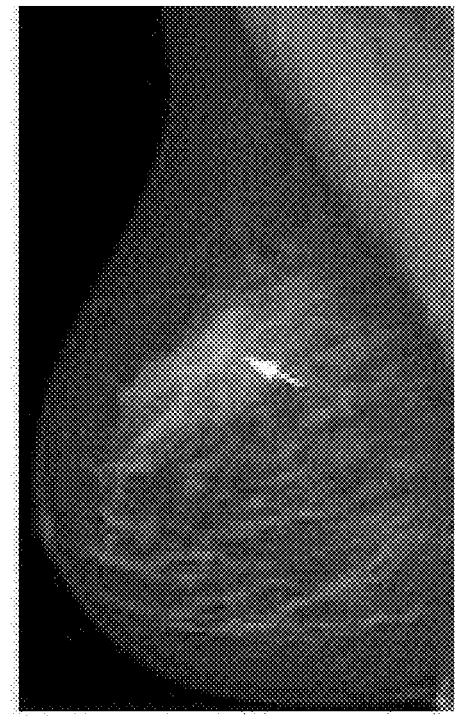
Figure 18C:
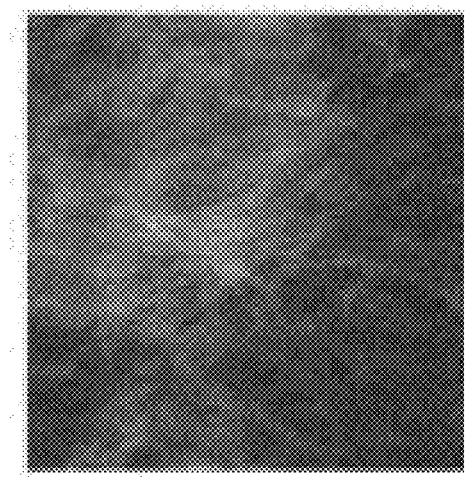

FIGS. 18A, 18B, and 18C show how the photon counting technology may be utilized in Mammography. FIGS. 18A, 18B, and 18C show two-view screening mammograms obtained with a direct radiography photon-counting system that show a spiculated mass in the right upper quadrants (arrow). The diagnosis was invasive ductal carcinoma, 8 mm in diameter, as seen on the right craniocaudal image (FIG. 18A), right mediolateral oblique image (FIG. 18B), and a zoomed in craniocaudal image of the lesion (FIG. 18C). (Weigel, S., Berkemeyer, S., Girnus, R., Sommer, A., Lenzen, H., & Heindel, W. (2014). Digital Mammography Screening with Photon-counting Technique: Can a High Diagnostic Performance Be Realized at Low Mean Glandular Dose? Radiology, 271(2), 345-355. doi:10.1148/radiol.13131181).

Indeed, it is appreciated that the system and its individual components can include additional features and components, though not disclosed herein, while still preserving the principles of the present disclosure. Note also that the base computer can be one of any number devices, including a desktop or laptop computer, etc.

Aspects of the present disclosure may be embodied in other specific forms without departing from its spirit or essential characteristics. The described embodiments are to be considered in all respects only as illustrative, not restrictive. All changes that come within the meaning and range of equivalency of the claims are to be embraced within their scope.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While there have been shown, described and pointed out, fundamental features of the present disclosure as applied to the exemplary embodiments thereof, it will be understood that various omissions and substitutions and changes in the form and details of compositions, devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

What is claimed is:

1. A cabinet X-ray image system for obtaining X-ray images and colorized or grey scale density X-ray images of a specimen, the system comprising:
    a cabinet defining an interior chamber wherein the cabinet comprises a walled enclosure surrounding the interior chamber, a door configured to cover the interior chamber and a sampling chamber for containing the specimen;
    a display;
    an X-ray system including:
        an X-ray source;
        a photon counting X-ray detector; and
        a specimen platform; and
    a controller configured to:
        selectively energize the X-ray source to emit X-rays through the specimen to the photon counting X-ray detector;
        control the photon counting X-ray detector to collect a projection X-ray image of the specimen when the X-ray source is energized;
        determine the density of different areas of the specimen from data collected from the photon counting X-ray detector of the projection X-ray image of the specimen when the X-ray source is energized;
        create a density X-ray image of the specimen wherein the different areas of the specimen are indicated as a density or range of densities based on the determined density of different areas of the specimen; and
        selectively display the density X-ray image of the specimen on the display.

2. The cabinet X-ray image system of claim 1, wherein the data collected from the photon counting X-ray detector comprises a number of photons impinging on the photon counting X-ray detector.

3. The cabinet X-ray image system of claim 1, wherein the data collected from the photon counting X-ray detector comprises an intensity of photons impinging on the photon counting X-ray detector.

4. The cabinet X-ray image system of claim 1, wherein the photon-counting detector comprises one or more of photomultipliers, Geiger counters, single-photon avalanche diodes, superconducting nanowire single-photon detectors, transition edge sensors, CCD, scintillation counters, and hybrid pixel photon counting detectors.

5. The cabinet X-ray image system of claim 1, wherein the different areas of the specimen indicated as a density or range of densities are displayed in different grey scales, different colors or different shades of color.

6. The cabinet X-ray image system of claim 1, wherein the specimen platform is configured for excised tissue, organ or bone specimens.

7. The cabinet X-ray image system of claim 1, wherein the specimen platform is configured for any organic or inorganic specimen that fits inside an X-ray cabinet.

8. The cabinet X-ray image system of claim 1, wherein the cabinet X-ray image system further includes:
    an optical camera configured to capture an optical image of the specimen; and
    the controller is further configured to:
        control the optical camera system to capture and collect the optical image of the specimen; and
        selectively display the density X-ray image and the optical image of the specimen on the display.

9. The cabinet X-ray image system of claim 8, wherein the density X-ray image and the optical image of the specimen are displayed overlaid.

10. The cabinet X-ray image system of claim 1, wherein the different areas of the specimen of the density X-ray image are displayed in different grey scale, different color or different shades of color.

11. A cabinet X-ray image system for obtaining colorized or grey scale density tomosynthetic images of a specimen, the system comprising:
    a cabinet defining an interior chamber;
    a display;
    an X-ray system including:
        an X-ray source;
        a photon counting X-ray detector; and
        a specimen platform;
    a motion control mechanism positioned in the interior chamber and configured for moving the X-ray source to or along a plurality of positions within the interior chamber relative to the specimen disposed on the specimen platform; and
    a controller configured to:
        selectively energize the X-ray source to emit X-rays through the specimen to the photon counting X-ray detector at selected positions of the X-ray source relative to the specimen such that the isocenter of the emitted X-rays at the selected positions is located at a surface of the photon counting X-ray detector;
        control the photon counting X-ray detector to collect projection X-ray images of the specimen when the X-ray source is energized at the selected positions, wherein one of the projection X-ray images is a two-dimensional X-ray image taken at standard imaging angle of approximately 0°;
        determine the density of different areas of the specimen from data collected from the photon counting X-ray detector of each of the collection of the projection X-ray images of the specimen collected when the X-ray source is energized;
        create a collection of density projections X-ray images of the specimen wherein the density of different areas of the specimen is based on the determined density of different areas of the specimen for each of the collection of projection X-ray images;
        create a density tomosynthetic X-ray image reconstructed from the collection of density projection X-ray images using the determined density of different areas of the specimen for the projection X-ray images;
        process the determined density of different areas of the specimen for the collection of the projection X-ray images in the controller into one or more reconstructed density tomosynthetic X-ray images representing a volume of the specimen and relating to one or more image planes that are selectively the same or different from that of the two-dimensional X-ray image; and
selectively display the one or more reconstructed density tomosynthetic X-ray images on the display.

12. The cabinet X-ray image system of claim 11, wherein the data collected from the photon counting X-ray detector comprises a number of photons impinging on the photon counting X-ray detector.

13. The cabinet X-ray image system of claim 11, wherein data collected from the photon counting X-ray detector comprises an intensity of photons impinging on the photon counting X-ray detector.

14. The cabinet X-ray image system of claim 11, wherein the photon-counting detector comprises one or more of photomultipliers, Geiger counters, single-photon avalanche diodes, superconducting nanowire single-photon detectors, transition edge sensors, CCD, scintillation counters, and hybrid pixel photon counting detectors.

15. The cabinet X-ray image system of claim 11, wherein the density of different areas of the specimen is displayed in different grey scales, different colors or different shades of color.

16. The cabinet X-ray image system of claim 11, wherein the cabinet comprises a walled enclosure surrounding the interior chamber, a door configured to cover the interior chamber and a sampling chamber within the interior chamber for containing the specimen.

17. The cabinet X-ray image system of claim 11, wherein the specimen platform is configured for excised tissue, organ or bone specimens.

18. The cabinet X-ray image system of claim 11, wherein the specimen platform is configured for any organic or inorganic specimen that fits inside an X-ray cabinet.

19. The cabinet X-ray image system of claim 11, wherein the cabinet X-ray image system further includes:
an optical camera configured to capture an optical image of the specimen; and
the controller is further configured to:
control the optical camera system to capture and collect the optical image of the specimen; and
selectively display the one or more reconstructed density tomosynthetic X-ray images and the optical image of the specimen on the display.

20. The cabinet X-ray image system of claim 19, wherein the one or more reconstructed density tomosynthetic X-ray images and the optical image of the specimen are displayed overlaid.

21. The cabinet X-ray image system of claim 11, wherein the different areas of the specimen of the one or more reconstructed density tomosynthetic X-ray images are displayed in different grey scale, different color or different shades of color.

22. A method for obtaining X-ray images and colorized or grey scale density X-ray images of a specimen using a cabinet X-ray image system, wherein the cabinet X-ray image system comprises:
a cabinet defining an interior chamber wherein the cabinet comprises a walled enclosure surrounding the interior chamber, a door configured to cover the interior chamber and a sampling chamber for containing the specimen;
a display;
an X-ray system including:
an X-ray source;
a photon counting X-ray detector; and
a specimen platform; and
a controller;
wherein the method comprises using the controller to:
selectively energize the X-ray source to emit X-rays through the specimen to the photon counting X-ray detector;
control the photon counting X-ray detector to collect an X-ray image of the specimen when the X-ray source is energized;
determine the density of different areas of the specimen from data collected from the photon counting X-ray detector of the projection X-ray image of the specimen when the X-ray source is energized;
create a density X-ray image of the specimen wherein the different areas of the specimen are indicated as a density or range of densities based on the determined density of different areas of the specimen; and
selectively display the density X-ray image of the specimen on the display.

23. The method of claim 22, wherein the data collected from the photon counting X-ray detector comprises a number of photons impinging on the photon counting X-ray detector.

24. The method of claim 22, wherein the data collected from the photon counting X-ray detector comprises an intensity of photons impinging on the photon counting X-ray detector.

25. The method of claim 22, wherein the cabinet X-ray image system further includes:
an optical camera configured to capture an optical image of the specimen;
wherein the controller is configured to:
control the optical camera system to capture and collect the optical image of the specimen; and
selectively display the density X-ray image and the optical image of the specimen on the display; and
the method further includes
controlling the optical camera system to capture and collect the optical image of the specimen; and
selectively displaying the density X-ray image and the optical image of the specimen on the display.

26. The method of claim 25, wherein the density X-ray image and the optical image of the specimen are displayed overlaid.

27. A method for obtaining X-ray images and colorized or grey scale density X-ray images of a specimen using a cabinet X-ray image system, wherein the cabinet X-ray image system comprises:
a cabinet defining an interior chamber wherein the cabinet comprises a walled enclosure surrounding the interior chamber, a door configured to cover the interior chamber and a sampling chamber for containing the specimen;
a display;
an X-ray system including:
an X-ray source;
a photon counting X-ray detector; and
a specimen platform; and
a controller configured to:
selectively energize the X-ray source to emit X-rays through the specimen to the photon counting X-ray detector;
control the photon counting X-ray detector to collect a projection X-ray image of the specimen when the X-ray source is energized;
determine the density of different areas of the specimen from data collected from the photon counting X-ray detector of the projection X-ray image of the specimen when the X-ray source is energized;

create a density X-ray image of the specimen wherein the different areas of the specimen are indicated as a density or range of densities based on the determined density of different areas of the specimen; and selectively display the density X-ray image of the specimen on the display;

wherein the method comprises:

controlling the X-ray detector to collect an X-ray image of the specimen when the X-ray source is energized;

determining the density of different areas of the specimen from data collected from the photon counting X-ray detector of the projection X-ray image of the specimen when the X-ray source is energized;

creating a density X-ray image of the specimen wherein the different areas of the specimen are indicated as a density or range of densities based on the determined density of different areas of the specimen; and selectively displaying the density X-ray image of the specimen on the display.

28. The method of claim 27, wherein the data collected from the photon counting X-ray detector comprises a number of photons impinging on the photon counting X-ray detector.

29. The method of claim 27, wherein the data collected from the photon counting X-ray detector comprises an intensity of photons impinging on the photon counting X-ray detector.

30. The method of claim 27, wherein the cabinet X-ray image system further includes:

an optical camera configured to capture an optical image of the specimen;

the controller is further configured to:

control the optical camera system to capture and collect the optical image of the specimen; and selectively display the density X-ray image and the optical image of the specimen on the display; and the method further includes controlling the optical camera system to capture and collect the optical image of the specimen; and selectively displaying the density X-ray image and the optical image of the specimen on the display.

* * * * *